(12) United States Patent
Ide

(10) Patent No.: US 10,285,576 B2
(45) Date of Patent: May 14, 2019

(54) ENDOSCOPE ANTIFOGGING UNIT AND ENDOSCOPE SYSTEM

(71) Applicant: OLYMPUS CORPORATION, Tokyo (JP)

(72) Inventor: Takayuki Ide, Akishima (JP)

(73) Assignee: OLYMPUS CORPORATION, Tokyo (JP)

(*) Notice: Subject to any disclaimer, the term of this patent is extended or adjusted under 35 U.S.C. 154(b) by 296 days.

(21) Appl. No.: 15/270,205

(22) Filed: Sep. 20, 2016

(65) Prior Publication Data
US 2017/0007110 A1    Jan. 12, 2017

Related U.S. Application Data

(63) Continuation of application No. PCT/JP2015/056228, filed on Mar. 3, 2015.

(30) Foreign Application Priority Data

Apr. 7, 2014 (JP) .................... 2014-078923

(51) Int. Cl.
*A61B 1/00* (2006.01)
*A61B 1/12* (2006.01)
(Continued)

(52) U.S. Cl.
CPC .......... *A61B 1/127* (2013.01); *A61B 1/00096* (2013.01); *A61B 1/04* (2013.01);
(Continued)

(58) Field of Classification Search
CPC ..... A61B 1/027; A61B 1/028; A61B 1/00096; G02B 23/2484; G02B 23/2423; G02B 27/0006

See application file for complete search history.

(56) References Cited

U.S. PATENT DOCUMENTS

2010/0016671 A1* 1/2010 Wieters ............... A61B 1/0008
                                                   600/169
2010/0309553 A1* 12/2010 Nagamizu ............. A61B 1/04
                                                   359/512
(Continued)

FOREIGN PATENT DOCUMENTS

CN    102292014 A    12/2011
CN    103874450 A     6/2014
(Continued)

OTHER PUBLICATIONS

Chinese Office Action dated Jul. 11, 2017 in Chinese Patent Application No. 201580016208.5.
(Continued)

*Primary Examiner* — John P Leubecker
(74) *Attorney, Agent, or Firm* — Scully, Scott, Murphy & Presser, P.C.

(57) ABSTRACT

In a state in which a heat generator and a temperature sensor are disposed on a wiring board, a measurement wiring is disposed in a vicinity of the heat generator, or the temperature sensor is disposed in a vicinity of a heat-generation wiring. A suppressing portion is disposed in either a first heat transfer path extending from the heat generator to the measurement wiring or a second heat transfer path extending from the heat-generation wiring to the temperature sensor. The suppressing portion suppresses heat transfer from the heat generator to the measurement wiring in the first heat transfer path, or suppresses heat transfer from the heat-generation wiring to the temperature sensor in the second heat transfer path.

9 Claims, 13 Drawing Sheets

(51) Int. Cl.
  *A61B 1/05* (2006.01)
  *G02B 23/24* (2006.01)
  *G02B 27/00* (2006.01)
  *A61B 1/04* (2006.01)

(52) U.S. Cl.
  CPC .............. *A61B 1/05* (2013.01); *A61B 1/128* (2013.01); *G02B 23/2423* (2013.01); *G02B 27/0006* (2013.01)

(56) References Cited

U.S. PATENT DOCUMENTS

| | | | |
|---|---|---|---|
| 2011/0092769 A1 | 4/2011 | Kokubo | |
| 2011/0301414 A1* | 12/2011 | Hotto | A61B 1/00009 600/114 |
| 2013/0303853 A1* | 11/2013 | Takahashi | A61B 1/00114 600/134 |
| 2013/0310644 A1* | 11/2013 | Ichimura | A61B 1/127 600/109 |
| 2014/0088366 A1* | 3/2014 | Solingen | A61B 1/00135 600/169 |
| 2014/0142384 A1* | 5/2014 | Chung | A61B 1/128 600/112 |
| 2014/0221743 A1 | 8/2014 | Sugiyama | |

FOREIGN PATENT DOCUMENTS

| | | | |
|---|---|---|---|
| JP | 2013-081656 A | 5/2013 | |
| JP | 2014-155583 A | 8/2014 | |
| WO | WO 2010/055753 A1 | 5/2010 | |
| WO | WO 2013/054819 A1 | 4/2013 | |
| WO | WO 2014106913 A1 * | 7/2014 | ........... A61B 1/0008 |
| WO | WO 2014125850 A1 * | 8/2014 | ........... A61B 1/0008 |

OTHER PUBLICATIONS

International Search Report dated Jun. 2, 2015 issued in corresponding International Patent Application No. PCT/JP2015/056228.

English translation of International Preliminary Report on Patentability dated Oct. 20, 2016 together with the Written Opinion received in related International Application No. PCT/JP2015/056228.

\* cited by examiner

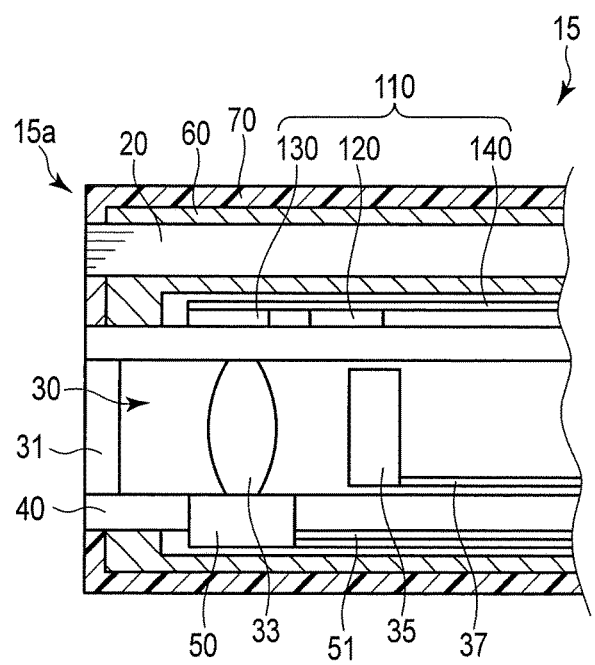
F I G. 2
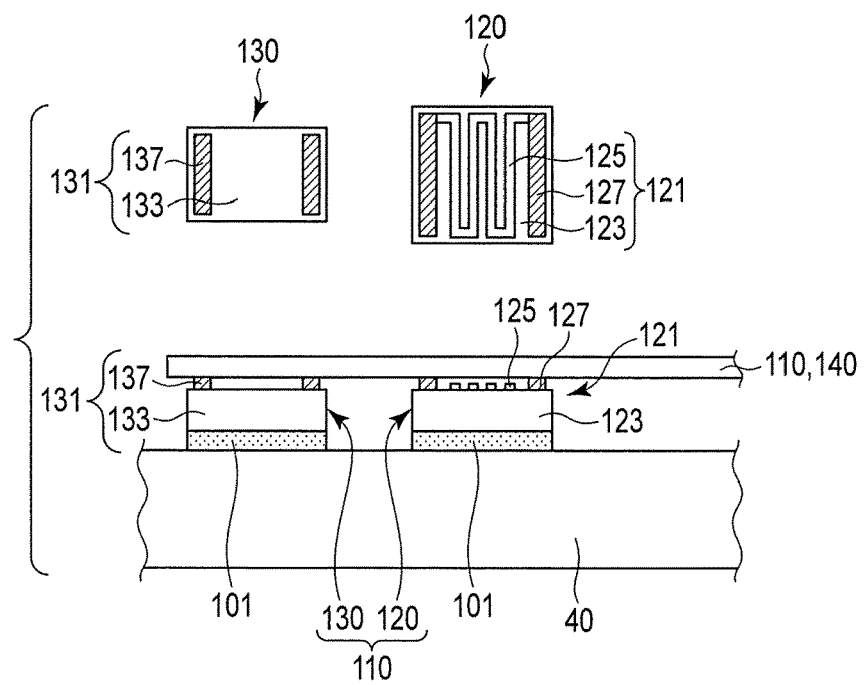
F I G. 3

4B-4B

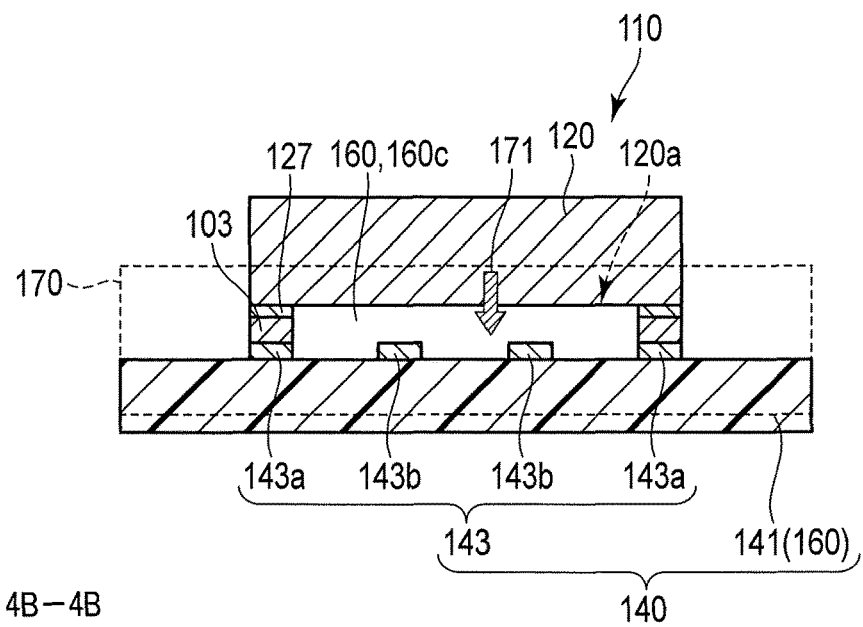
F I G. 4E
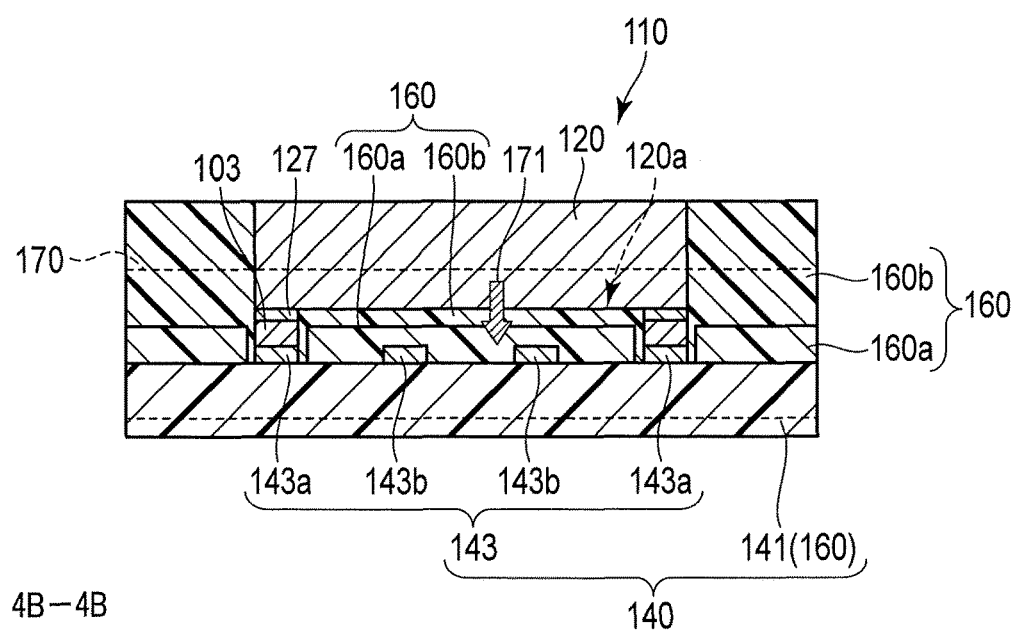
F I G. 4F

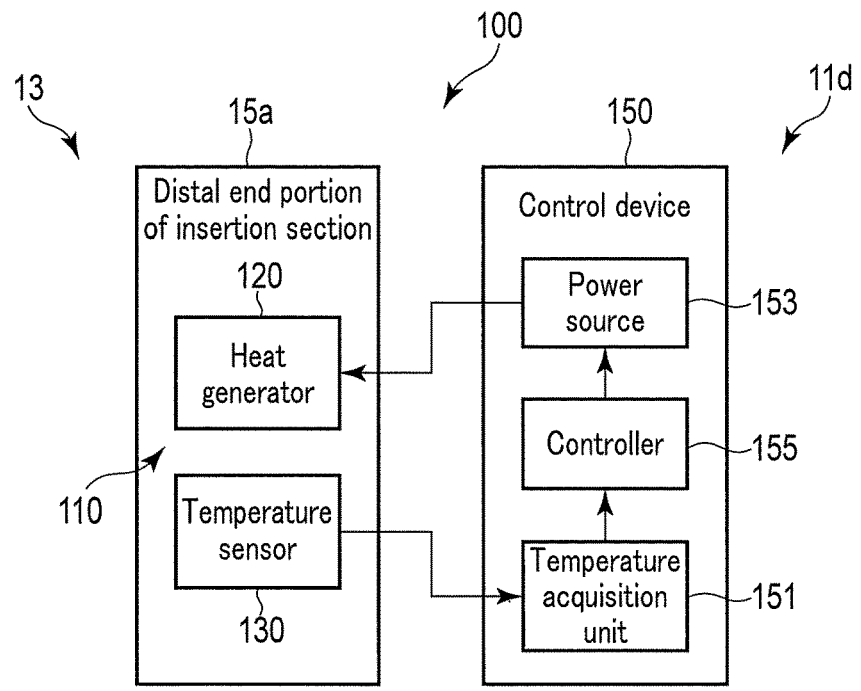
F I G. 6
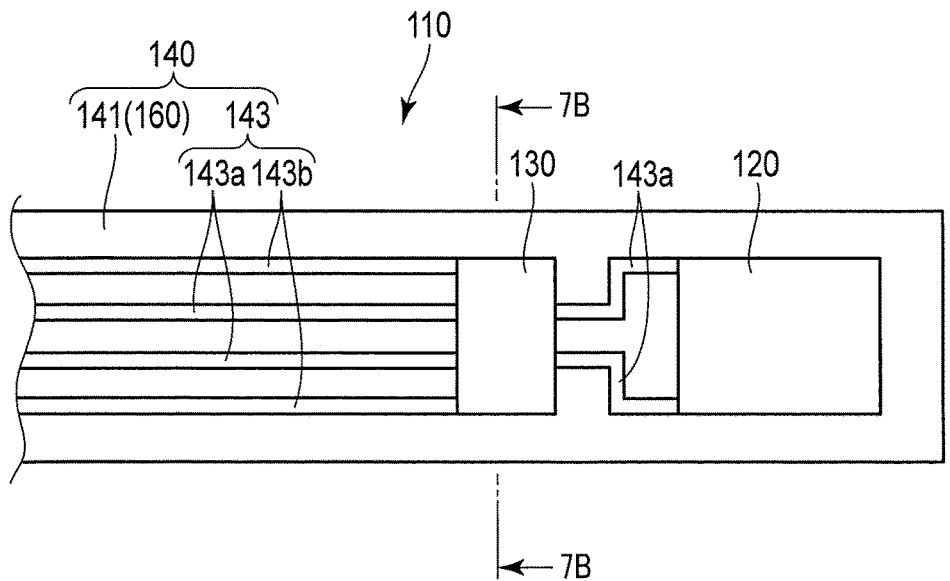
F I G. 7A

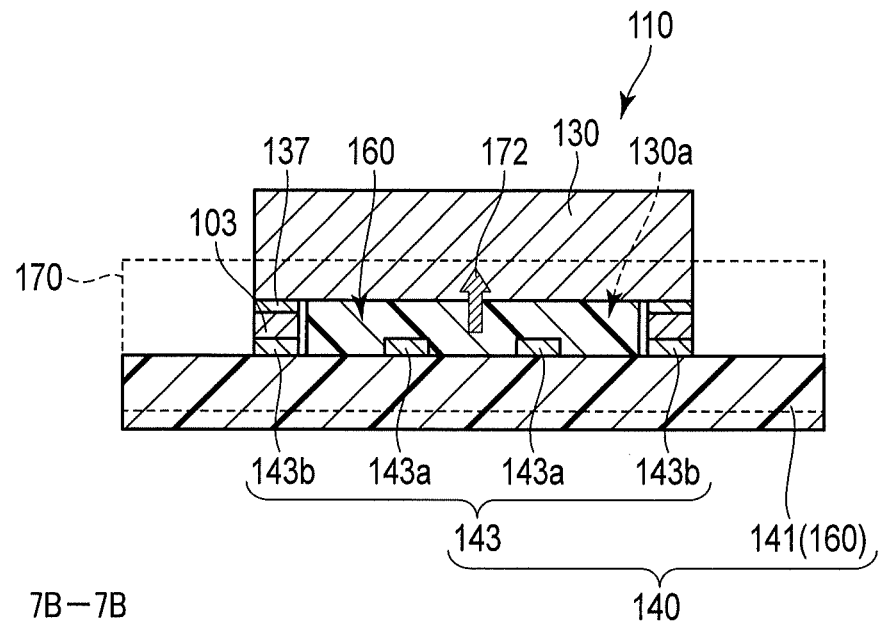
F I G. 7B
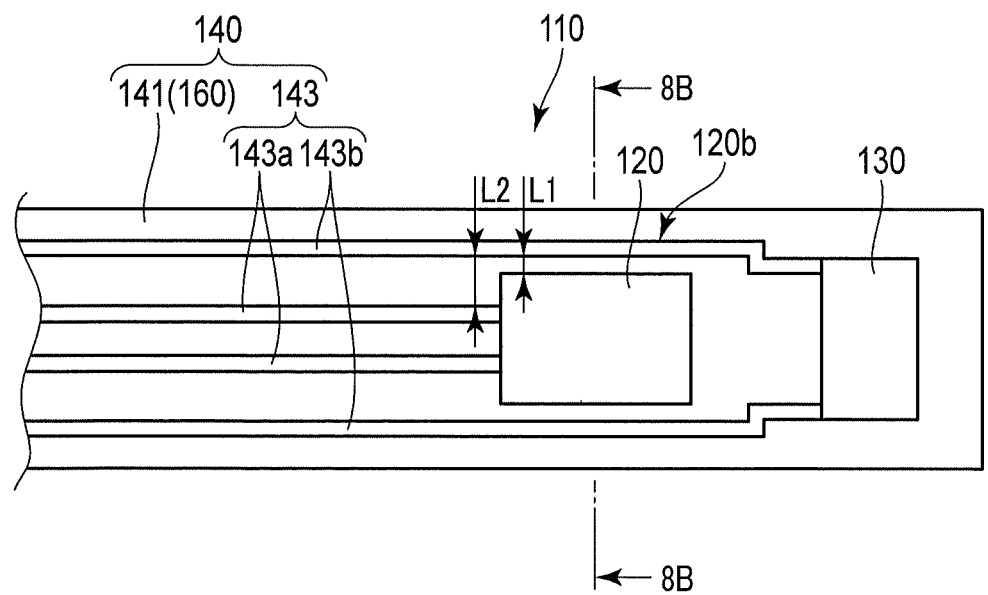
F I G. 8A

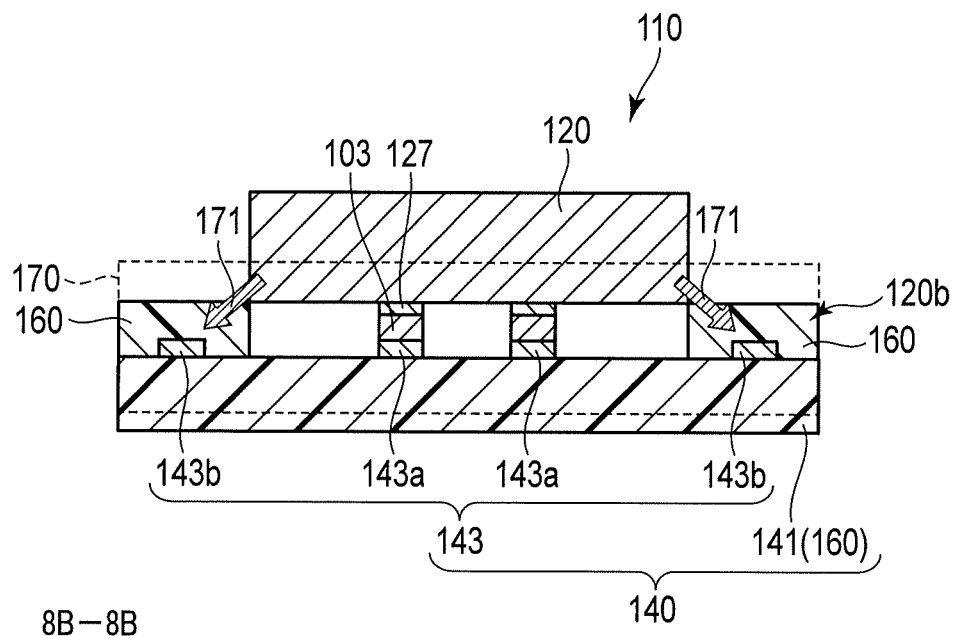
F I G. 8B
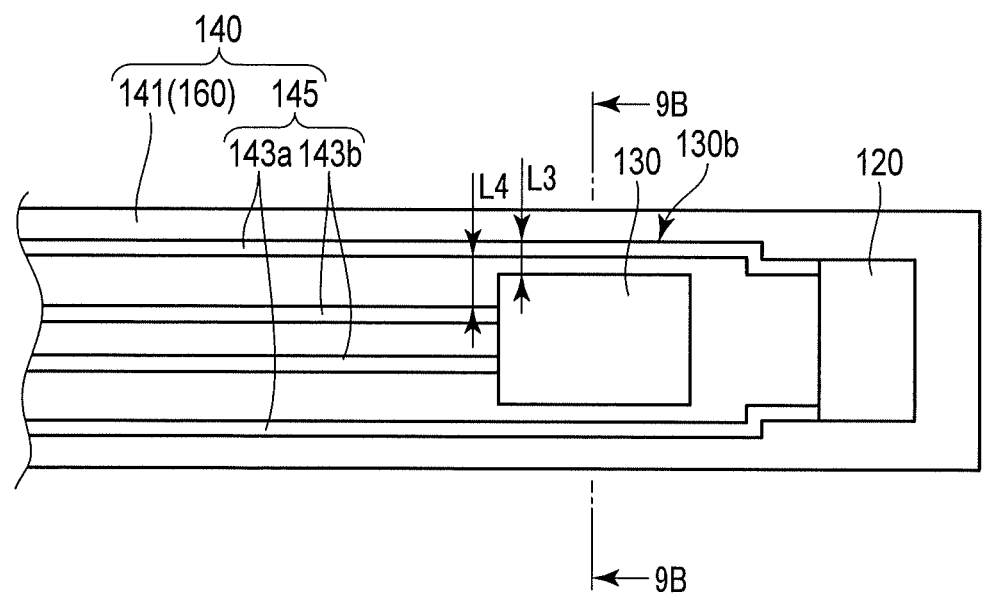
F I G. 9A

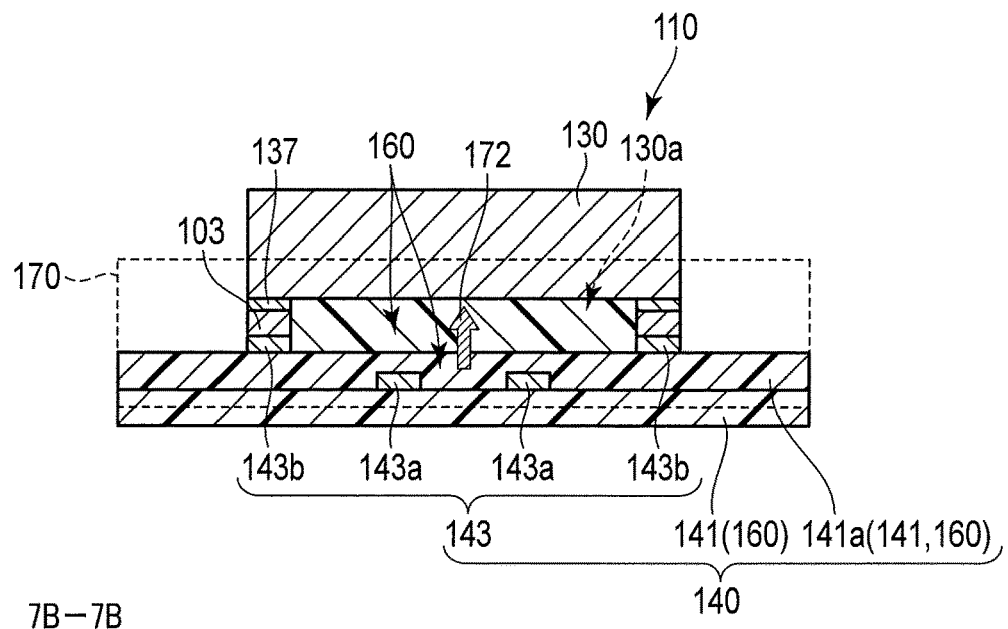
F I G. 10B
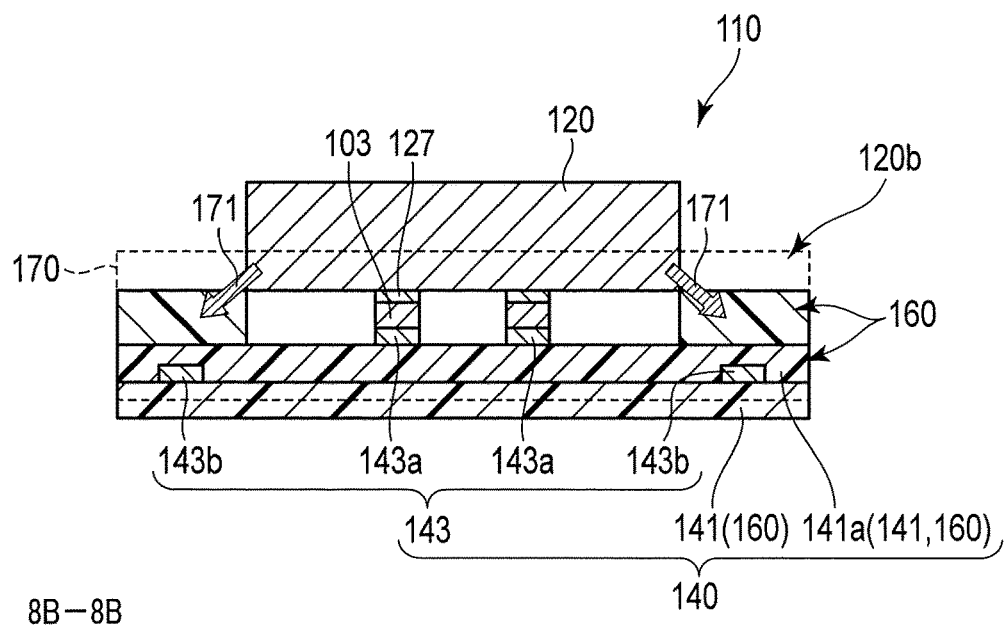
F I G. 10C

ENDOSCOPE ANTIFOGGING UNIT AND ENDOSCOPE SYSTEM

CROSS-REFERENCE TO RELATED APPLICATIONS

This application is a Continuation Application of PCT Application No. PCT/JP2015/056228, filed Mar. 3, 2015 and based upon and claiming the benefit of priority from prior Japanese Patent Application No. 2014-078923, filed Apr. 7, 2014, the entire contents of all of which are incorporated herein by reference.

BACKGROUND OF THE INVENTION

1. Field of the Invention

The present invention relates to an endoscope antifogging unit and an endoscope system.

2. Description of the Related Art

For example, an endoscope antifogging unit disclosed in Jpn. Pat. Appln. KOKAI Publication No. 2013-81656 includes a heat generator, a temperature sensor, and a wiring board on which the heat generator and the temperature sensor are mounted. The heat generator and temperature sensor are attached to a heat transfer member. The heat transfer member is heated by the heat generator, and the temperature of the heat transfer member is measured by the temperature sensor. The wiring board includes a heat-generation wiring which is connected to the heat generator, and a measurement wiring which is connected to the temperature sensor. The heat resistance between locations where the heat generator and temperature sensor are in close proximity is higher than the heat resistance between the heat generator and heat transfer member and the heat resistance between the temperature sensor and heat transfer member. Thereby, since the direct thermal effect from the heat generator upon the temperature sensor is reduced, the accuracy of measurement at a time when the temperature sensor measures the temperature of the heat transfer member is enhanced.

BRIEF SUMMARY OF THE INVENTION

An aspect of an endoscope antifogging unit of the invention is disposed in an inside of a distal end portion of an endoscope insertion section and is configured to prevent fogging occurring on an optical member disposed in the inside of the distal end portion, the endoscope antifogging unit includes a heat generator configured to heat the inside by heat generation; a temperature sensor configured to measure a temperature in the inside; a wiring board including a base layer, and wirings disposed on the base layer and including a heat-generation wiring connected to the heat generator and a measurement wiring connected to the temperature sensor, and wherein the wiring board being configured such that, in a state in which the heat generator and the temperature sensor are disposed on the wiring board, the measurement wiring is disposed in a vicinity of the heat generator, or the temperature sensor is disposed in a vicinity of the heat-generation wiring; and a suppressing portion disposed in either a first heat transfer path extending from the heat generator to the measurement wiring or a second heat transfer path extending from the heat-generation wiring to the temperature sensor, and wherein the suppressing portion configured to suppress heat transfer from the heat generator to the measurement wiring in the first heat transfer path, or to suppress heat transfer from the heat-generation wiring to the temperature sensor in the second heat transfer path.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a view illustrating an internal configuration of a distal end portion of an insertion section of an endoscope.

FIG. 3 is a view illustrating the configuration of an endoscope antifogging unit.

FIG. 4E is a cross-sectional view taken along line 4B-4B, illustrating an example of the suppressing portion.

FIG. 4F is a cross-sectional view taken along line 4B-4B, illustrating an example of the suppressing portion.

FIG. 6 is a view illustrating configurations 1 and 2 of an antifogging system of the endoscope.

FIG. 7A is a top view of an endoscope antifogging unit in a first modification of the first embodiment.

FIG. 7B is a cross-sectional view taken along line 7B-7B shown in FIG. 7A.

FIG. 8A is a top view of an endoscope antifogging unit in a second modification of the first embodiment.

FIG. 8B is a cross-sectional view taken along line 8B-8B shown in FIG. 8A.

FIG. 9A is a top view of an endoscope antifogging unit in a third modification of the first embodiment.

FIG. 10B is a cross-sectional view taken along line 7B-7B, illustrating a first modification of the second embodiment.

FIG. 10C is a cross-sectional view taken along line 8B-8B, illustrating a second modification of the second embodiment.

DETAILED DESCRIPTION OF THE INVENTION

Hereinafter, embodiments of the present invention will be described in detail with reference to the accompanying drawings. Incidentally, for example, in some drawings, depiction of some of members is omitted for the purpose of clearer illustration.

First Embodiment

[Configuration]

A first embodiment is described with reference to FIG. 1, FIG. 2, FIG. 3, FIG. 4A, FIG. 4B, FIG. 4C, FIG. 4D, FIG. 4E, FIG. 4F, FIG. 4G, FIG. 4H, FIG. 5A, FIG. 5B, FIG. 5C, and FIG. 6.

[Endoscope System 10]

Figure 1:
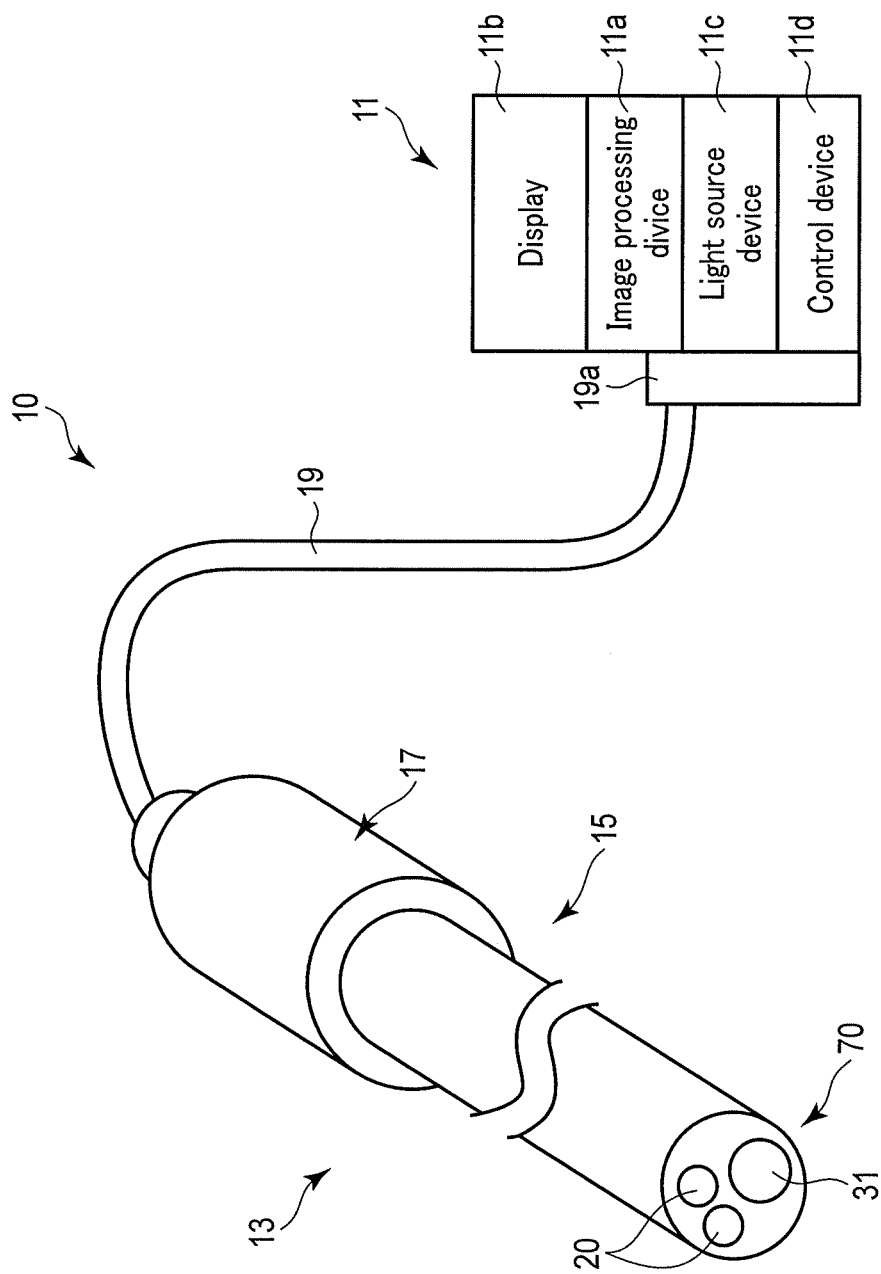
FIG. 1 is a schematic view of an endoscope system according to a first embodiment of the present invention.

As illustrated in FIG. 1, an endoscope system 10 includes a peripheral equipment 11 of an endoscope 13, and the endoscope 13 which is connected to the peripheral equipment 11.

[Peripheral Equipment 11]

As illustrated in FIG. 1, the peripheral equipment 11 includes an image processing device 11a, a display 11b, a light source device 11c, and a control device 11d.

The image processing device 11a image-processes an image captured by an imager 35 (see FIG. 2) of the endoscope 13.

The display 11b displays an image which was image-processed by the image processing device 11a.

The light source device 11c emits illumination light.

The control device 11d controls the image processing device 11a, display 11b, light source device 11c, and endoscope 13.

[Endoscope 13] The endoscope 13 as illustrated in FIG. 1 functions, for example, as a rigid scope. The endoscope 13 includes, for example, a hollow, elongated insertion section 15 which is inserted into a lumen such as a body cavity; an operation section 17 which is disposed at a proximal end portion of the insertion section 15 and operates the insertion section 15; and a universal cord 19 connected to the operation section 17. The universal cord 19 includes a coupling connector 19a for detachable connection to the peripheral equipment 11.

[Configuration of Distal End Portion 15a of Endoscope 13]

As illustrated in FIG. 2, a distal end portion 15a of the insertion section 15 includes a light guide 20 which guides the illumination light and radiates the illumination light to an observation target; and an imaging unit 30 which images the observation target. The distal end portion 15a further includes a lens frame 40 which holds the imaging unit 30; and a driving circuit 50 which is disposed on the lens frame 40, drives a lens 33 of the imaging unit 30, and executes focusing or zooming.

The light guide 20 is connected to the light source device 11c through the insertion section 15, operation section 17, universal cord 19 and coupling connector 19a, thereby, the illustration light is supplied to the light guide 20. In addition, the light guide 20 emits the illumination light to the outside from a distal end portion of the light guide 20.

The imaging unit 30 includes a lens cover 31 which is disposed in the inside of the distal end portion 15a such that the lens cover 31 is exposed to the outside from the distal end face of the distal end portion 15a; and the lens 33 which is disposed behind the lens cover 31. The imaging unit 30 further includes an imager 35 which is disposed behind the lens 33, and an imaging cable 37 which is connected to the imager 35 and supplies power to the imager 35. The imaging cable 37 transmits a control signal, which controls the imager 35, to the imager 35, and transmits a video signal captured by the imager 35.

The imaging cable 37 is inserted up to the coupling connector 19a via the insertion section 15, operation section 17 and universal cord 19. By the coupling connector 19a being connected to the control device 11d which controls the endoscope 13, the imaging cable 37 is connected to the control device 11d. Thereby, the power and control signal for driving the imager 35 are supplied to the imaging cable 37. In addition, the imaging cable 37 supplies and transmits the power and control signal to the imager 35. By the coupling connector 19a being connected to the control device 11d, the video signal captured by the imager 35 is transmitted to the image processing device 11a via the control device 11d.

In the meantime, the lens cover 31 may not be a simple plate-shaped cover member, but may have a form of a lens. In the description below, at least one of the lens cover 31 and lens 33 of the distal end portion 15a, the fogging of which is prevented when the insertion section 15 is inserted in the body cavity or the like, is referred to as "optical member". It should suffice if the optical member is disposed in the inside of the distal end portion 15a, for example, such that the optical member is exposed to the outside from the distal end face of the distal end portion 15a.

The driving circuit 50 includes, for example, a motor or the like. The driving circuit 50 is connected to a driving cable 51 which supplies the power to the driving circuit 50 and transmits a driving signal, which drives the driving circuit 50, to the driving circuit 50.

The driving cable 51 is inserted up to the coupling connector 19a via the insertion section 15, operation section 17 and universal cord 19. By the coupling connector 19a being connected to the control device 11d, the driving cable 51 is connected to the control device 11d. Thereby, the power and control signal for driving the driving circuit 50 are supplied to the driving cable 51. In addition, the driving cable 51 supplies the power and control signal to the driving circuit 50.

The lens frame 40 is formed of, for example, a cylindrical member. The lens frame 40 holds the imaging unit 30 including the optical member, such that the imaging unit 30 is accommodated in the cylinder.

As illustrated in FIG. 2, the distal end portion 15a of the insertion section 15 further includes an inner frame 60 which is disposed in the inside of the distal end portion 15a and holds the light guide 20 and lens frame 40; and an outer frame 70 which covers the inner frame 60 and functions as an outermost layer of the distal end portion 15a.

The inner frame 60 is formed of, for example, a metal, and the outer frame 70 is formed of, for example, a resin.

The lens frame 40 and inner frame 60 function as a heat transfer member that transfers heat, which is generated from a heat generator 120, to the optical member.

[Fogging of Optical Member]

In usual cases, the endoscope 13 including the above-described distal end portion 15a is installed, for example, in a treatment room in an environment in which temperatures and humidity are controlled. Thus, the distal end portion 15a, before use, is exposed to such temperatures and humidity. When the insertion section 15 is inserted in the body cavity, fogging occurs on the optical member such as the lens cover 31 due to, for example, a temperature difference between room temperature and body temperature, or a high humidity environment (humidity: about 98 to about 100%) in the body cavity, and the view field for imaging considerably deteriorates.

[Configuration 1 (Antifogging Unit 110) of Endoscope Antifogging System 100]

Thus, as illustrated in FIG. 6, the endoscope 13 and the control device 11d for controlling the endoscope 13 are equipped with an endoscope antifogging system 100 which prevents fogging of the endoscope 13. As illustrated in FIG. 2, FIG. 3 and FIG. 6, the endoscope antifogging system 100 includes an endoscope antifogging unit (hereinafter referred to as "antifogging unit 110") which is disposed in the inside of the distal end portion 15a of the insertion section 15 and prevents fogging which occurs on the optical member disposed in the inside of the distal end portion 15a.

As illustrated in FIG. 2 and FIG. 3, the antifogging unit 110 includes, for example, the heat generator 120 and a temperature sensor 130, which are disposed on the lens frame 40. In order to prevent fogging occurring on the optical member such as the lens cover 31, the heat generator 120 heats, by heat generation, the inside of the distal end portion 15a including the lens cover 31 via the lens frame 40. The temperature sensor 130 measures, via the lens frame 40, the temperature of the inside of the distal end portion 15a including the lens cover 31. The heat generator 120 includes a heater. The antifogging unit 110 further includes a flexible wiring board 140. The heat generator 120 and the temperature sensor 130 are mounted on the wiring board 140 by, for example, a surface mounting technique or the like.

As illustrated in FIG. 3, in the antifogging unit 110, for example, back surfaces of the heat generator 120 and temperature sensor 130 are bonded to, for example, an outer peripheral surface of the lens frame 40 by, for example, an adhesive 101 with a high coefficient of thermal conductivity. The adhesive 101 may be configured such that an adhesive with a lower coefficient of thermal conductivity is coated with a very small thickness. In the meantime, as illustrated in FIG. 2, it should suffice if the heat generator 120 and temperature sensor 130 are disposed in the inside of the distal end portion 15a. Thus, the heat generator 120 and temperature sensor 130 may be disposed, for example, in the inner frame 60 which holds a lens unit. The lens unit includes, for example, the lens cover 31, the lens 33, and the lens frame 40 which holds the lens cover 31 and lens 33. In this manner, the antifogging unit 110 is disposed such that the heat generator 120 and temperature sensor 130 are mounted in the lens frame 40 or inner frame 60, which functions as the heat transfer member. As illustrated in FIG. 2 and FIG. 3, the heat generator 120 and the temperature sensor 130 are mounted on the wiring board 140 by the surface mounting technique or the like. The wiring board 140 is connected to a lead line (not shown). The lead line supplies power and control signals, which drive the heat generator 120 and the temperature sensor 130, to the heat generator 120 and the temperature sensor 130 via the wiring board 140, and transmits detection data which was detected by the temperature sensor 130. The lead line is inserted up to the coupling connector 19a via the insertion section 15, operation section 17 and universal cord 19. By the coupling connector 19a being connected to the control device 11d, the lead line is connected to the control device 11d. Thereby, the lead line supplies the power and control signals to the heat generator 120 and the temperature sensor 130. By the coupling connector 19a being connected to the control device 11d, temperature data, which is included in the detection data detected by the temperature sensor 130, is transmitted to the control device 11d.

As illustrated in FIG. 2 and FIG. 3, for example, the heat generator 120 is disposed so as to neighbor the temperature sensor 130 in a longitudinal-axis direction of the distal end portion 15a. For example, the heat generator 120 is disposed at a desired distance farther from the temperature sensor 130. For example, the heat generator 120 is disposed farther from the lens cover 31 (the distal end face of the distal end portion 15a) than the temperature sensor 130.

[Heat Generator 120]

The heat generator 120 heats the inside of the distal end portion 15a at such a temperature that the temperature of the lens cover 31 becomes higher than the body temperature and no heat injury is caused on a living body tissue. This temperature is, for example, about 38° C. or above, and about 42° C. or below. In addition, the heat generator 120 heats the inside of the distal end portion 15a such that the optical member is set at this temperature. Incidentally, the heat generator 120 may directly heat the optical member, or may indirectly heat the optical member via, for example, the lens frame 40 or inner frame 60.

As illustrated in FIG. 3, the heat generator 120 includes, for example, a heat generating chip 121. The heat generating chip 121 includes, for example, a ceramic substrate 123, a metallic resistor 125 disposed on the substrate 123, and pads 127 disposed on the substrate 123 and electrically connected to the metallic resistor 125. The metallic resistor 125 is formed in a thin film form or a paste form, and functions as a heat generating body. The pads 127 are formed as current introduction terminals. The heat generating chip 121 may be formed as a resistor body composed of a bulk which is formed in a chip shape, for example, by baking a resistive material. In the description below, the bulk refers to a body formed in a chip shape, for example, by baking a material in this manner.

[Temperature Sensor 130]

The temperature sensor 130 measures the temperature of the inside of the distal end portion 15a.

As illustrated in FIG. 3, the temperature sensor 130 includes, for example, a temperature sensor chip 131. The temperature sensor chip 131 includes, for example, a thermistor body 133 formed of a bulk, and pads 137 which are disposed on the thermistor body 133 and electrically connected to the thermistor body 133. The thermistor body 133 functions as a temperature-measuring body. The pads 137 are formed as current introduction terminals. Like the heat generating chip 121, the temperature sensor chip 131 may be formed with a ceramic substrate used as a base body, or a thermistor resistor or a metallic resistor may be formed in a thin-film or paste form on the ceramic substrate.

[Wiring Board 140]

As illustrated in FIG. 4A, FIG. 4B, FIG. 4C, FIG. 4D, FIG. 4E, FIG. 4F, FIG. 4G and FIG. 4H, the wiring board 140 includes a base layer 141, and wirings 143 which are provided on the base layer 141. The wirings 143 include heat-generation wirings 143a which are connected to the heat generator 120, and measurement wirings 143b which are connected to the temperature sensor 130.

[Base Layer 141]

The base layer 141 is formed of, for example, a resin such as polyimide, such that the base layer 141 has a low coefficient of thermal conductivity. In the meantime, the base layer 141 has an electrical insulation property. Specifically, the base layer 141 serves also as an insulation member.

[Wirings 143]

In the wirings 143, the heat-generation wirings 143a and measurement wirings 143b are disposed on the base layer 141, and are disposed on a plane in common in the base layer 141. Since the heat-generation wirings 143a and measurement wirings 143b are formed of, for example, copper foil, the heat-generation wirings 143a and measurement wirings 143b have high coefficients of thermal conductivity.

As illustrated in FIG. 4C, FIG. 4D, FIG. 4E, FIG. 4F and FIG. 4G, one end portion of the heat-generation wiring 143a is bonded to the pad 127 of the heat generator 120 by, for example, a bonding material 103 such as solder. Thereby, the heat generator 120 is electrically connected to the heat-generation wiring 143a. The one end portion comprising the bonding material 103 and the pad 127 functions as an electrical connection portion between the heat generator 120 and the heat-generation wiring 143a.

Figure 4A:
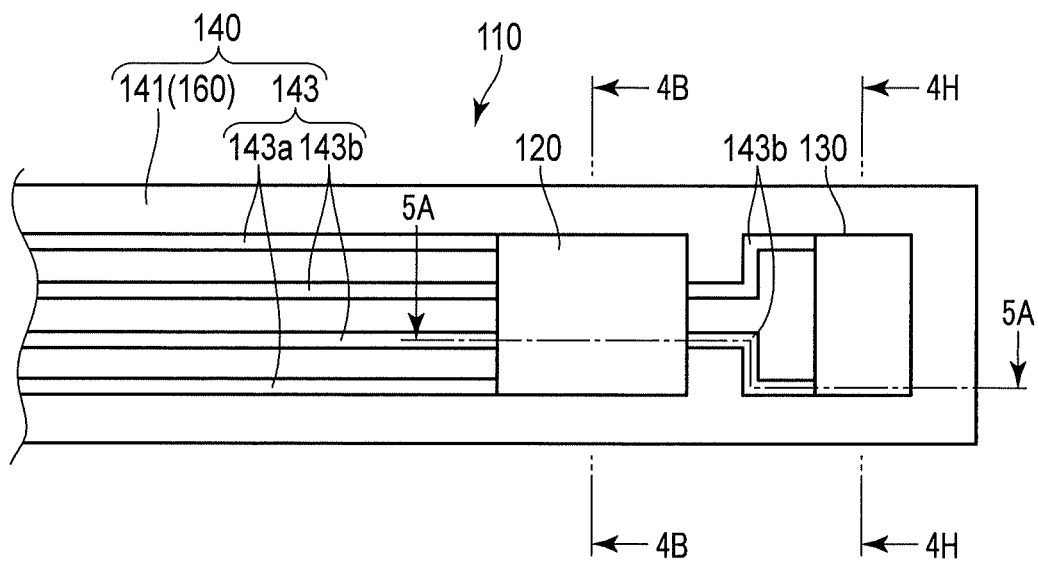
FIG. 4A is a top view of the endoscope antifogging unit.
Figure 4B:
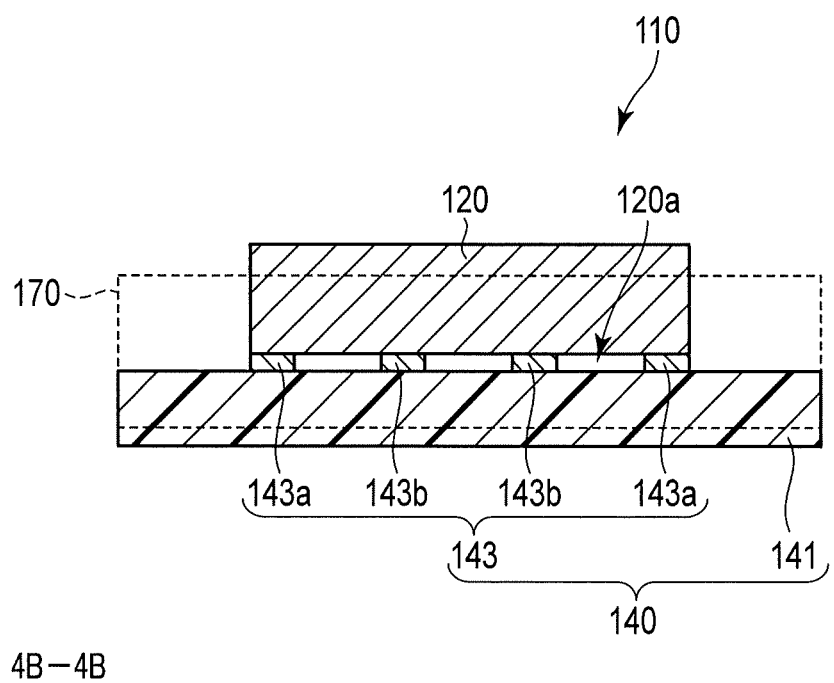
FIG. 4B is a cross-sectional view taken along line 4B-4B shown in FIG. 4A in a state in which a suppressing portion is not provided, FIG. 4B being a view for describing the vicinity of a heat generator.
Figure 4C:
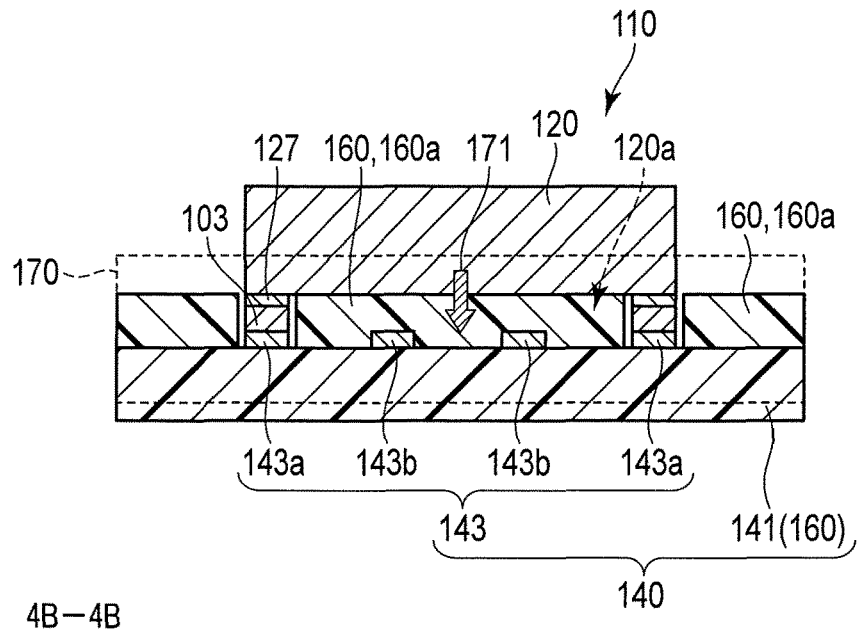
FIG. 4C is a cross-sectional view taken along line 4B-4B, illustrating an example of a suppressing portion.
Figure 4D:
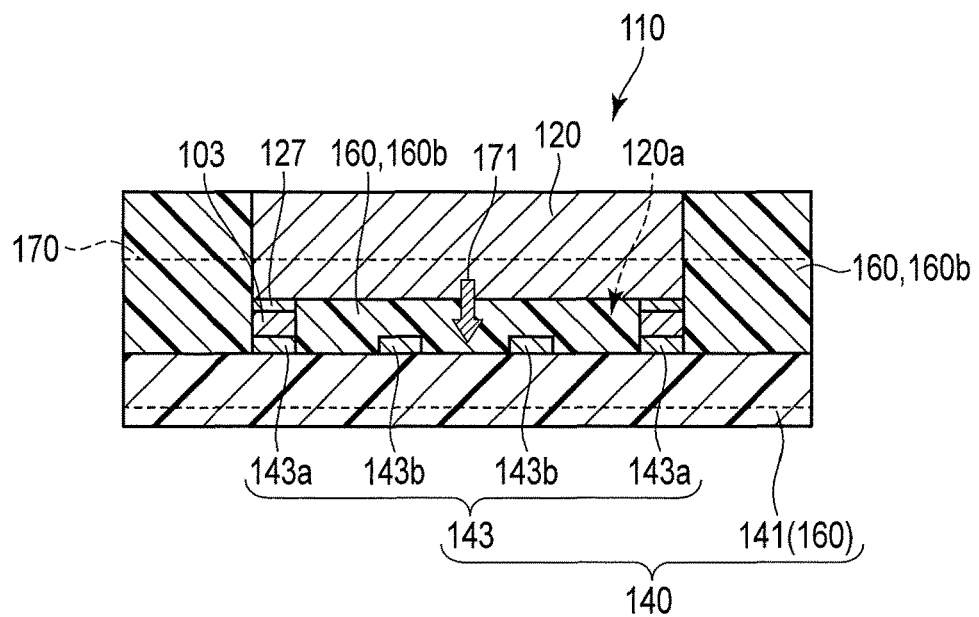
FIG. 4D is a cross-sectional view taken along line 4B-4B, illustrating an example of the suppressing portion.
Figure 4G:
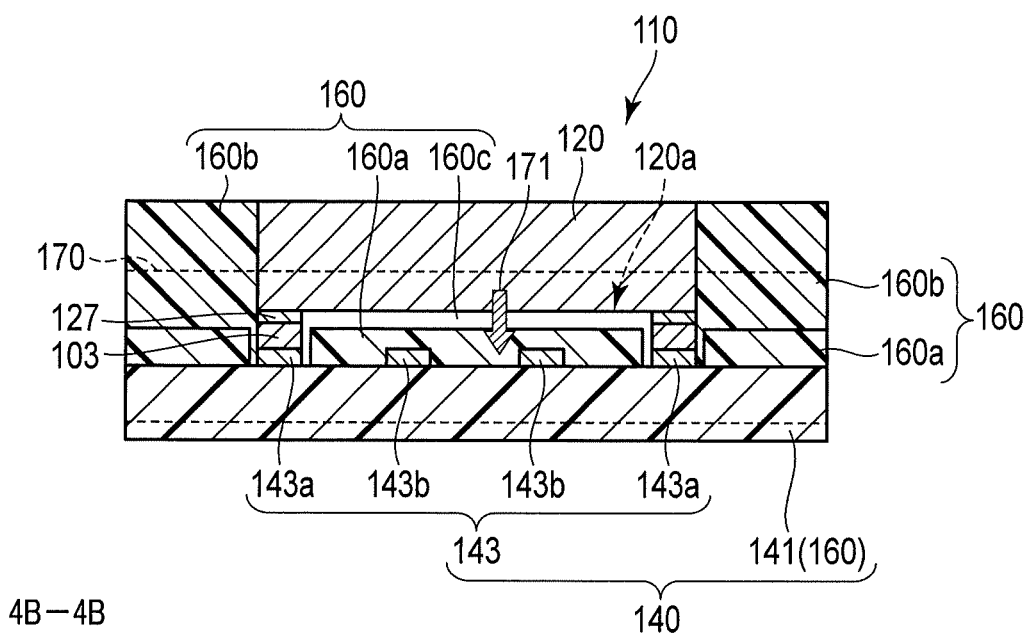
FIG. 4G is a cross-sectional view taken along line 4B-4B, illustrating an example of the suppressing portion.
Figure 4H:
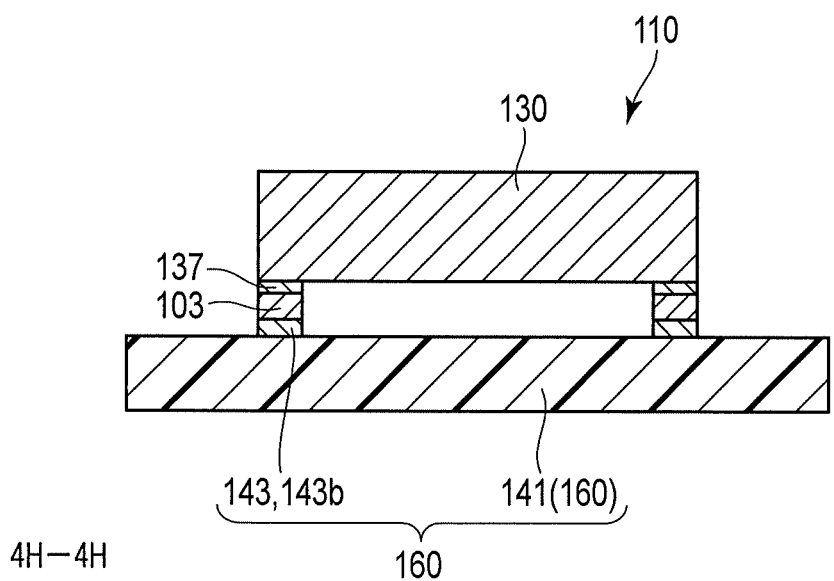
FIG. 4H is a cross-sectional view taken along 4H-4H shown in FIG. 4A.

As illustrated in FIG. 4H, one end portion of the measurement wiring 143b is bonded to the pad 137 of the temperature sensor 130 by, for example, a bonding material 103 such as solder. Thereby, the temperature sensor 130 is electrically connected to the measurement wiring 143b. The one end portion comprising the bonding material 103 and the pad 137 functions as an electrical connection portion between the temperature sensor 130 and the measurement wiring 143b.

The other end portion of the heat-generation wiring 143a and the other end portion of the measurement wiring 143b functions as exposed lead portions. These other end portions are connected to the above-described lead line (not shown). The lead line is inserted up to the coupling connector 19a via the insertion section 15, operation section 17 and universal cord 19. By the coupling connector 19a being connected to the control device 11d, the wirings 143 are connected to the control device 11d. Thereby, the power and control signal, which drive the heat generator 120, are supplied to the heat generator 120 via the lead line and heat-generation wirings 143a. The power and control signal, which drive the temperature sensor 130, are supplied to the temperature sensor 130 via the lead line and measurement wirings 143b. By the coupling connector 19a being connected to the control device 11d, temperature data, which is included in the detection data detected by the temperature sensor 130, is transmitted to the control device 11a via the measurement wirings 143b and lead line.

[Positions of Heat-Generation Wring Portions 143a and Measurement Wirings 143b]

As illustrated in FIG. 4A, the heat-generation wirings 143a and measurement wirings 143b are disposed in the longitudinal direction of the wiring board 140. In addition, the heat-generation wirings 143a are disposed in parallel to the measurement wirings 143b.

As illustrated in FIG. 4A, for example, the heat-generation wirings 143a include two wiring lines, and the measurement wirings 143b include two wiring lines which are different from the wiring lines of the heat-generation wirings 143a. In this manner, the heat-generation wirings 143a and the measurement wirings 143b are mutually different systems.

In the present embodiment, as illustrated in FIG. 4B, etc., as regards the thus disposed heat-generation wirings 143a, measurement wirings 143b, wiring substrate portion 140, heat generator 120 and temperature sensor 130, the measurement wirings 143b are disposed in the vicinity of the heat generator 120 in the state in which the heat generator 120 and temperature sensor 130 are disposed on the wiring substrate portion 140.

As illustrated in FIG. 4B, etc., the vicinity of the heat generator 120 refers to, for example, an inside of a desired range of the heat generator 120, such as a range 170 of transfer of heat generated from the heat generator 120, and, to be more specific, the peripheral area of the heat generator 120. In other words, the measurement wirings 143b are disposed on the wiring board 140 at a position where heat generated from the heat generator 120 is transferred.

Next, an example of the vicinity of the heat generator 120 in the present embodiment is described.

As described above, and as illustrated in FIG. 3 and FIG. 4A, for example, the heat generator 120 is disposed farther from the lens cover 31 (the distal end face of the distal end portion 15a) than the temperature sensor 130.

In this case, as illustrated in FIG. 4A, for example, the two wiring lines of the measurement wirings 143b are disposed to be sandwiched between one wiring line and another wiring line of the heat-generation wiring lines 143a in the width direction of the wiring board 140. For example, in the width direction of the wiring board 140, the distance between the wiring lines of the measurement wirings 143b, the distance between one wiring line of the heat-generation wirings 143a and one wiring line of the measurement wirings 143b, which neighbors this one wiring line of the heat-generation wirings 143a, and the distance between the other wiring line of the heat-generation wirings 143a and the other wiring line of the measurement wirings 143b, which neighbors this other wiring line of the heat-generation wirings 143a, are substantially equal to each other.

The heat-generation wirings 143a and the measurement wirings 143b, which are disposed as described above, are disposed symmetric with respect to a center axis of the heat generator 120 which is disposed along the longitudinal direction of the wiring board 140.

As illustrated in FIG. 4A and FIG. 4B, a part of the measurement wiring 143b is disposed in the vicinity of the heat generator 120, and extends to the temperature sensor 130.

As illustrated in FIG. 4B, in the present embodiment, a part of the measurement wiring 143b is disposed below the heat generator 120 in the thickness direction of the wiring board 140, Specifically, is disposed in a heat-generating-side directly under portion 120a which is disposed directly under the heat generator 120, to be more specific, is disposed between the heat generator 120 and the wiring board 140.

The heat-generating-side directly under portion 120a is included in the above-described vicinity of the heat generator 120, for example, is located in the range 170 of transfer of heat generated from the heat generator 120, and is located in the peripheral area of the heat generator 120. In other words, the measurement wiring 143b is disposed at a position where heat generated from the heat generator 120 is transferred, and the heat generated from the heat generator 120 is conveyed to the measurement wiring 143b.

[Measurement Accuracy of Temperature Sensor 130]

Figure 5A:
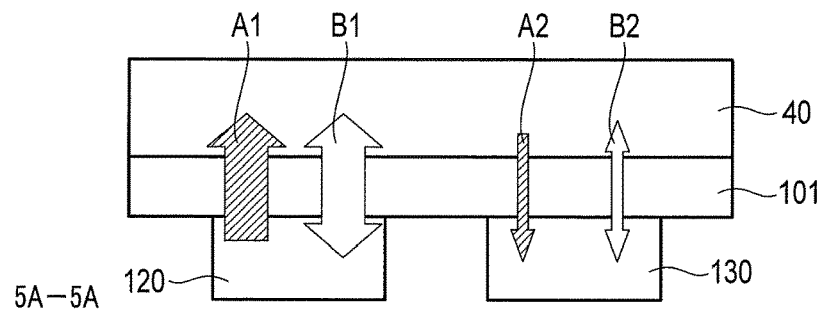
FIG. 5A is a cross-sectional view taken along line 5A-5A shown in FIG. 4A in a state in which a wiring board is not provided, FIG. 5A being a view for describing heat flows and temperature differences between respective members.
Figure 5B:
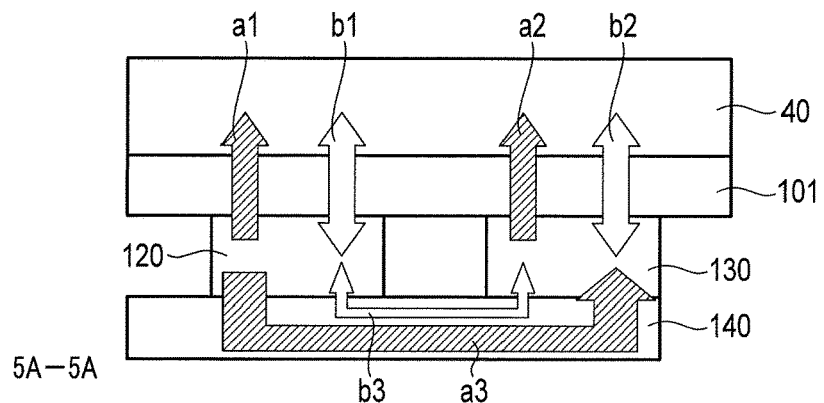
FIG. 5B is a cross-sectional view taken along line 5A-5A shown in FIG. 4A in a state in which a wiring board is provided, FIG. 5B being a view for describing heat flows and temperature differences between respective members.

A description is given of heat flows and temperature differences between respective members in an imagined ideal case in which the wiring board 140 is not provided as illustrated in FIG. 5A, and in a case in which the wiring board 140 is actually provided as illustrated in FIG. 5B. Incidentally, the thickness of arrows indicates a relative magnitude. In the description below, for the purpose of easier description, the heat radiated to spaces other than members is ignored.

As illustrated in FIG. 5A, when the wiring board 140 is not provided, the heat generated from the heat generator 120 is conveyed (flows) only to the lens frame 40, which is the heat transfer member, via the adhesive 101. Thus, a heat flow A1, which is conveyed (flows) to the lens frame 40 from the heat generator 120 via the adhesive 101, becomes large. Since the heat flow A1 is large, a temperature difference B1 between the heat generator 120 and lens frame 40 becomes large due to the adhesive 101.

By contrast, a heat flow A2 hardly occurs, which is conveyed to the temperature sensor 130 via the adhesive 101 from the lens frame 40 that does not generate heat. Thus, a temperature difference B2 between the lens frame 40 and temperature sensor 130 becomes small, and the temperature of the temperature sensor 130 becomes substantially equal to the temperature of the lens frame 40.

In this manner, the heat generated from the heat generator 120 exerts hardly any direct influence upon the temperature sensor 130, and it can be said that the measurement accuracy of the temperature sensor 130 is high.

As illustrated in FIG. 5B, when the wiring board 140 is provided, the heat generated from the heat generator 120 is conveyed to the lens frame 40, which is the heat transfer member, via the adhesive 101. In this case, the heat is further conveyed to the temperature sensor 130 via the wiring board 140. Thus, a heat flow a1, which is conveyed to the lens frame 40 from the heat generator 120 via the adhesive 101, becomes smaller than the heat flow A1. Since the heat flow a1 is smaller than the heat flow A1, a temperature difference b1 between the heat generator 120 and lens frame 40 becomes smaller than the temperature difference B1.

In FIG. 5B, a heat flow a3 occurs, which is conveyed from the heat generator 120 to the temperature sensor 130 via the wiring board 140. Here, the wirings 143 of the wiring board 140 are formed of copper foil or the like with a high coefficient of thermal conductivity. Unlike the present embodiment, a case is now assumed that the wiring board 140 is formed of a material such as ceramic with a high coefficient of thermal conductivity. In this case, by the heat flow a3 and the wiring board 140 with the high coefficient of thermal conductivity, a temperature difference b3 occurs between the heat generator 120 and temperature sensor 130. In this case, since the coefficient of thermal conductivity of the wiring board 140 is high, the temperature difference b3 becomes small, and the temperature of the heat generator 120 becomes substantially equal to the temperature of the temperature sensor 130.

If the temperature of the heat generator 120 becomes substantially equal to the temperature of the temperature sensor 130, as described above, a heat flow a2 occurs, which is conveyed from the temperature sensor 130 to the lens frame 40 via the adhesive 101. The direction of the heat flow a2 is opposite to the direction of the heat flow A2, and the heat flow a2 is larger than the heat flow A2. Due to the heat flow a2 and the adhesive 101, a temperature difference b2 between the lens frame 40 and temperature sensor 130 becomes larger than the temperature difference B2.

In this manner, when the wiring board 140 is disposed, a large difference occurs between the temperature of the lens frame 40 and the temperature of the temperature sensor 130, and the measurement accuracy of the temperature sensor 130 lowers.

Therefore, it is required to prevent a decrease in measurement accuracy of the antifogging unit 110.

[Suppressing Portion 160]

As illustrated in FIG. 4C, FIG. 4D, FIG. 4E, FIG. 4F and FIG. 4G, taking the above-described decrease in measurement accuracy into account, the antifogging unit 110 includes a suppressing portion 160 which suppresses heat transfer from the heat generator 120 to the temperature sensor 130 via the measurement wirings 143$b$ and wiring board 140. Thus, the heat resistance of the suppressing portion 160 is large, and, in other words, the coefficient of thermal conductivity of the suppressing portion 160 is low.

In particular, in this embodiment, since a part of the measurement wiring 143$b$ is disposed in the heat-generating-side directly under portion 120$a$, the suppressing portion 160 needs to suppress the transfer of heat, which is generated from the heat generator 120, to the part of the measurement wiring 143$b$.

Thus, as illustrated in FIG. 4C, FIG. 4D, FIG. 4E, FIG. 4F and FIG. 4G, the suppressing portion 160 is disposed in a first heat transfer path 171 extending from the heat generator 120 to the measurement wirings 143$b$. The first heat transfer path 171 includes, for example, the heat-generating-side directly under portion 120$a$, and indicates a path along which the heat generated from the heat generator 120 reaches the measurement wirings 143$b$. The suppressing portion 160, which is disposed in the first heat transfer path 171, suppresses the heat transfer from the heat generator 120 to the measurement wirings 143$b$. Thereby, the suppressing portion 160 suppresses the transfer of the heat, which is generated from the heat generator 120, to the temperature sensor 130 via the wiring board 140 including the wirings 143.

Specifically, the suppressing portion 160 is formed by optimally setting the thickness of the wirings 143, the thickness of the pads 127 and the thickness of the bonding material 103. The suppressing portion 160 is formed by a member or the like with a low coefficient of thermal conductivity being interposed between the heat generator 120 and the measurement wirings 143$b$.

Figure 5C:
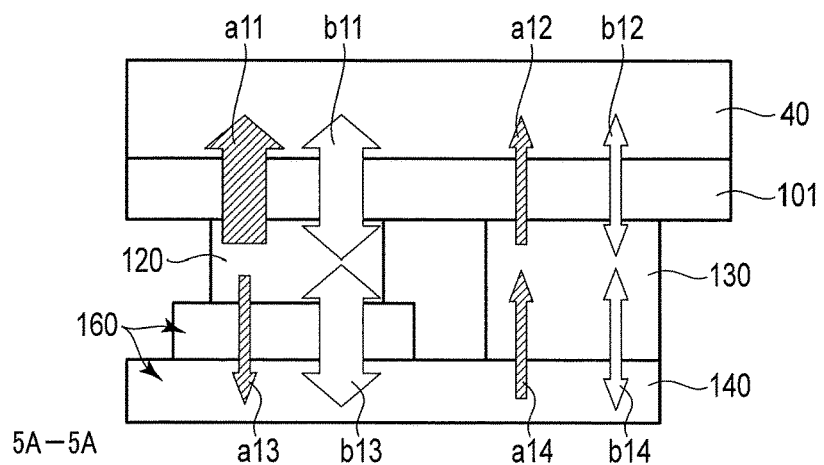
FIG. 5C is a cross-sectional view taken along line 5A-5A shown in FIG. 4A, FIG. 5C being a view for describing heat flows and temperature differences between respective members in the embodiment.

As illustrated in FIG. 5C, by the suppressing portion 160 disposed as described above, the heat resistance from the heat generator 120 to the wiring board 140 increases, and a heat flow a13, which is conveyed from the heat generator 120 to the wiring board 140 via the heat-generating-side directly under portion 120$a$, becomes smaller than the heat flow a3.

In addition, a temperature difference b13 occurs between the heat generator 120 and the wiring board 140. In this case, the temperature difference b13 is increased by the heat resistance of the suppressing portion 160.

By the suppressing portion 160, a heat flow a14, which is conveyed from the wiring board 140 to the temperature sensor 130, becomes smaller than the heat flow a3.

Accordingly, a temperature difference b14 between the wiring board 140 and the temperature sensor 130 becomes small.

A heat flow a12, which is conveyed from the temperature sensor 130 to the lens frame 40 via the adhesive 101, becomes smaller than the heat flow a2.

Thus, a temperature difference b12 between the temperature sensor 130 and the lens frame 40 becomes smaller than the temperature difference b2.

Specifically, the suppressing portion 160 decreases the direct influence of the heat, which is generated from the heat generator 120, upon the temperature sensor 130 via the wiring board 140, and the measurement accuracy of the temperature sensor 130 is enhanced.

Because of the above, the heat resistance of the heat transfer path from the heat generator 120 to the lens frame 40 is smaller than the heat resistance of the first heat transfer path 171. The heat resistance of the heat transfer path from the heat generator 120 to the temperature sensor 130 via the lens frame 40 is smaller than the heat resistance of the heat transfer path from the heat generator 120 to the temperature sensor 130 via the wiring board 140 including the measurement wirings 143b.

The above-described suppressing portion 160 includes at least one of the base layer 141 of the wiring board 140 (see FIG. 4A, FIG. 4C, FIG. 4D, FIG. 4E, FIG. 4F, FIG. 4G and FIG. 4H), a protection layer 160a which protects the surface of the wirings 143 in a manner to cover the surface of the wirings 143 (see FIG. 4C, FIG. 4F and FIG. 4G), a sealing portion 160b which seals the wirings 143 in a manner to cover the wirings 143 (see FIG. 4D, FIG. 4F and FIG. 4G), and an air layer 160c (see FIG. 4E and FIG. 4G).

As described above, the base layer 141 is formed of, for example, a resin such as polyimide, such that the coefficient of thermal conductivity of the base layer 141 becomes low.

The protection layer 160a is formed of, for example, a resin such as polyimide, such that the coefficient of thermal conductivity of the protection layer 160a becomes low. The protection layer 160a may be disposed around the wirings 143 in a manner to surround the wirings 143.

The sealing portion 160b includes, for example, an epoxy-based resin or a silicone-based resin, such that the coefficient of thermal conductivity of the sealing layer 160b becomes low. The sealing layer 160b has an electrical insulation property. Thus, as illustrated in FIG. 4D, FIG. 4F and FIG. 4G, the sealing portion 160b may be disposed around the heat generator 120, for example, in a manner to surround the heat generator 120 and to seal the heat generator 120.

The coefficient of thermal conductivity of the air layer 160c is low. The air layer 160c may communicate with the outside. As illustrated in FIG. 4G, the air layer 160c may be surrounded by the sealing portion 160b, and may be sealed by the sealing portion 160b.

Needless to say, as illustrated in FIG. 4F and FIG. 4G, there may be provided a combinational portion including at least two of the protection layer 160a, sealing portion 160b and air layer 160c.

[Configuration 2 (Control Device 150) of Endoscope Antifogging System 100]

As illustrated in FIG. 6, the endoscope antifogging system 100 further includes a control device 150 which controls the driving of the heat generator 120 based on the temperature of the inside of the distal end portion 15a measured by the temperature sensor 13. The control device 150 controls the temperature for preventing fogging of the optical member of the endoscope 13. The control device 150 is, for example, a separate body from the endoscope 13. The control device 150 is disposed, for example, in the control device 11d which controls the endoscope 13. Although the control device 150 is separate from the endoscope 13, the control device 150 may be mounted in the inside of the endoscope 13, such as in the operation section 17 of the endoscope 13.

As illustrated in FIG. 6, the control device 150 includes a temperature acquisition unit 151 which acquires an actual temperature of the inside of the distal end portion 15a measured by the temperature sensor 130; and a power source 153 which outputs to the heat generator 120 the power that is necessary for driving the heat generator 120 (hereinafter referred to as "driving power").

As illustrated in FIG. 6, the control device 150 further includes a controller 155 which calculates a difference between the temperature acquired by the temperature acquisition unit 151 and a preset target temperature, calculates, based on the calculated difference, such a driving power as to eliminate the difference, and controls the power source 153 so that the power source 153 may output this calculated driving power to the heat generator 120. The target temperature includes, for example, such a temperature as to prevent fogging of the optical member, such as the lens cover 31, by heating the optical member. The target temperature includes a temperature below such a degree that the temperature at the outer frame 70, which is the outermost layer of the distal end portion 15a, in particular, the temperature in the vicinity of the heat generator 120, may cause no heat injury to a living body tissue. In the meantime, the target temperature is, for example, desirably adjustable where necessary, by, for example, the control device 150. The target temperature is, for example, prerecorded in a recording unit (not shown) provided in the control device 150. The controller 155 has, for example, a hardware circuitry including ASCI.

The temperature, which is the acquisition result acquired by the temperature acquisition unit 151, is recorded in the recording unit (not shown). The temperature acquisition unit 151 acquires, for example, a desired timing, and a desired period and temperature. The temperature acquisition unit 151 has, for example, a hardware circuitry including ASCI.

The temperature measured by the temperature sensor 130 is fed back to the control device 150. By the feedback being repeated, the temperature in the inside of the distal end portion 15a is controlled with high accuracy such that the heating temperature of the heat generator 120 is set at the target temperature. Control methods of the heat generator 120 include, for example, ON-OFF control, PWM control, PID control, etc.

[Operation]

If the heat generator 120 generates heat, the heat generator 120 produces the heat radially around the heat generator 120. This heat, for example, tends to be conveyed from the heat generator 120 to the wiring board 140 including the measurement wirings 143b via the heat-generating-side directly under portion 120a.

However, in the present embodiment, the suppressing portion 160 is disposed in the heat-generating-side directly under portion 120a, and the suppressing portion 160 includes at least one of the protection layer 160a, sealing portion 160b and air layer 160c.

The suppressing portion 160, which is disposed in this manner, suppresses the transfer of heat to the measurement wirings 143b. Specifically, by the suppressing portion 160, the heat resistance from the heat generator 120 to the wiring board 140 via the heat-generating-side directly under portion 120a increases, and the heat flow a13 and heat flow a14 become smaller than the heat flow a3.

Moreover, since the heat flow a12 becomes smaller than the heat flow a2, the temperature difference b12 becomes smaller than the temperature difference b2.

Specifically, the suppressing portion 160 decreases the direct influence of the heat generated from the heat generator 120 upon the temperature sensor 130 via the wiring board 140, and the measurement accuracy of the temperature sensor 130 is enhanced.

The base layer 141 is formed of a resin, and the coefficient of thermal conductivity of the base layer 141 is low. The base layer 141 serves also as the suppressing portion 160, and, in other words, the suppressing portion 160 includes the base layer 141. Thus, even if the heat is conveyed to the base layer 141, the transfer of the heat from the base layer 141 to the measurement wirings 143b is suppressed, and the further transfer of the heat to the temperature sensor 130 is suppressed. As a result, the measurement accuracy of the temperature sensor 130 is enhanced.

[Advantageous Effects]

In this manner, in the present embodiment, in the state in which the measurement wirings 143b are disposed in the heat-generating-side directly under portion 120a included in the vicinity of the heat generator 120, the suppressing portion 160 is disposed in the heat-generating-side directly under portion 120a included in the first heat transfer path 171 extending from the heat generator 120 to the measurement wirings 143b, and the suppressing portion 160 suppresses heat transfer from the heat generator 120 to the measurement wirings 143b in the first heat transfer path 171.

Thereby, in the present embodiment, when the heat generator 120 generates heat, it is possible to suppress the transfer of the heat to the temperature sensor 130 via the measurement wirings 143b and wiring board 140. Therefore, in this embodiment, the measurement accuracy of the temperature sensor 130 can be enhanced.

In the present embodiment, the heat resistance of the heat transfer path from the heat generator 120 to the lens frame 40 is smaller than the heat resistance of the first heat transfer path 171. In this embodiment, the heat resistance of the heat transfer path from the heat generator 120 to the temperature sensor 130 via the lens frame 40 is smaller than the heat resistance of the heat transfer path from the heat generator 120 to the temperature sensor 130 via the wiring board 140 including the measurement wirings 143b.

Specifically, in this embodiment, since the suppressing portion 160 is disposed in the first heat transfer path 171, a great amount of heat can be suppressed by the suppressing portion 160, and it is possible to suppress the transfer of the heat, which is generated from the heat generator 120, to the first heat transfer path 171 than the lens frame 40.

In the present embodiment, the suppressing portion 160 is disposed in the heat-generating-side directly under portion 120a. Thus, when the heat generator 120 generates heat, it is possible to surely suppress the transfer of the heat to the temperature sensor 130 via the measurement wirings 143b and wiring board 140.

First Modification of the First Embodiment

Hereinafter, referring to FIG. 7A and FIG. 7B, a first modification of the first embodiment is described.

In the first embodiment, in the state in which the heat generator 120 and temperature sensor 130 are disposed on the wiring board 140, the measurement wirings 143b are disposed in the vicinity of the heat generator 120, and parts of the measurement wirings 143b are disposed in the heat-generating-side directly under portion 120a. However, this is not intended to be restrictive.

[Positions of Heat-Generation Wring Portions 143a and Measurement Wirings 143b]

In the state in which the heat generator 120 and temperature sensor 130 are disposed on the wiring board 140, the temperature sensor 130 may be disposed in the vicinity of the heat-generation wirings 143a.

As illustrated in FIG. 7B, etc., the vicinity of the heat-generation wirings 143a refers to, for example, an inside of a desired range of the heat-generation wirings 143a, such as a range 170 of transfer of heat generated from the heat-generation wirings 143a, and, to be more specific, the peripheral area of the heat-generation wirings 143a. In other words, the temperature sensor 130 is disposed on the wiring board 140 at a position where heat generated from the heat-generation wirings 143a is transferred.

Next, an example of the vicinity of the temperature sensor 130 in the present modification is described.

In this case, as illustrated in FIG. 7A, the positions of disposition of the heat generator 120 and temperature sensor 130 may be reversed, compared to the first embodiment. Thus, for example, the temperature sensor 130 is disposed farther from the lens cover 31 (the distal end face of the distal end portion 15a) than the heat generator 120.

In addition, as illustrated in FIG. 7A, for example, the two wiring lines of the heat-generation wirings 143a are disposed to be sandwiched between one wiring line and another wiring line of the measurement wiring lines 143b in the width direction of the wiring board 140. For example, in the width direction of the wiring board 140, the distance between the wiring lines of the heat-generation wirings 143a, the distance between one wiring line of the heat-generation wirings 143a and one wiring line of the measurement wirings 143b, which neighbors this one wiring line of the heat-generation wirings 143a, and the distance between the other wiring line of the heat-generation wirings 143a and the other wiring line of the measurement wirings 143b, which neighbors this other wiring line of the heat-generation wirings 143a, are substantially equal to each other.

The heat-generation wirings 143a and the measurement wirings 143b, which are disposed as described above, are disposed symmetric with respect to the center axis of the temperature sensor 130 which is disposed along the longitudinal direction of the wiring board 140.

As illustrated in FIG. 7B, in the thickness direction of the wiring board 140, a space portion is formed by the thickness of the measurement wirings 143b, etc., between the temperature sensor 130 and the wiring board 140. The heat-generation wirings 143a extend to the heat generator 120 through this space portion in the longitudinal direction of the wiring board 140.

As illustrated in FIG. 7B, this space portion functions as a measurement-side directly under portion 130a which is disposed directly under the temperature sensor 130. The measurement-side directly under portion 130a is included in the above-described vicinity of the temperature sensor 130, for example, is located in the range 170 of transfer of heat generated from the heat-generation wirings 143a, and is located in the peripheral area of the heat-generation wirings 143a. In other words, the measurement-side directly under portion 130a is disposed at a position where heat generated from the heat-generation wirings 143a is transferred, and the heat generated from the heat-generation wirings 143a is conveyed to the measurement-side directly under portion 130a.

Specifically, as illustrated in FIG. 7B, a part of the heat-generation wiring 143a is disposed below the temperature sensor 130 in the thickness direction of the wiring board 140, specifically, the part of the heat-generation wiring 143a is disposed in the measurement-side directly under portion 130a which is disposed directly under the temperature sensor 130, to be more specific, the part of the heat-generation wiring 143a is disposed between the temperature sensor 130 and wiring board 140. In the present modification, parts of the heat-generation wirings 143a are disposed directly under the temperature sensor 130, such that the space portion is formed between the heat-generation wirings 143a and the temperature sensor 130 in the thickness direction of the wiring board 140.

[Suppressing Portion 160]

In the present modification, since a part of the heat-generation wiring 143a is disposed in the measurement-side directly under portion 130a, the suppressing portion 160 needs to suppress the transfer of heat, which is generated from the heat-generation wiring 143a, to the temperature sensor 130.

Thus, as illustrated in FIG. 7B, the suppressing portion 160 is disposed in a second heat transfer path 172 extending from the heat-generation wirings 143a to the temperature sensor 130. The second heat transfer path 172 includes, for example, the measurement-side directly under portion 130a, and indicates a path along which the heat generated from the heat-generation wirings 143a reaches the temperature sensor 130. The suppressing portion 160, which is disposed in the second heat transfer path 172, suppresses the heat transfer from the heat-generation wirings 143a to the temperature sensor 130. Thereby, the suppressing portion 160 suppresses the transfer of the heat, which is generated from the heat-generation wirings 143a, to the temperature sensor 130.

By the above-described suppressing portion 160, the heat resistance from the heat-generation wirings 143a to the temperature sensor 130 via the measurement-side directly under portion 130a increases, and, in other words, the suppressing portion 160 suppresses the transfer of heat to the temperature sensor 130. Thereby, a heat flow, which is conveyed from the heat-generation wirings 143a to the temperature sensor 130 via the measurement-side directly under portion 130a, becomes smaller than the heat flow a3.

Furthermore, the heat flow a1t, which is conveyed from the temperature sensor 130 to the lens frame 40, becomes smaller than the heat flow a2. Thereby, the temperature difference b12 between the temperature sensor 130 and the lens frame 40 becomes smaller than the temperature difference b2.

Thus, the heat, which is generated from the heat generator 120, does not affect the temperature sensor 130, and the measurement accuracy of the temperature sensor 130 is enhanced.

Because of the above, the heat resistance of the heat transfer path from the heat generator 120 to the lens frame 40 is smaller than the heat resistance of the second heat transfer path 172. The heat resistance of the heat transfer path from the heat generator 120 to the temperature sensor 130 via the lens frame 40 is smaller than the heat resistance of the heat transfer path from the heat generator 120 to the temperature sensor 130 via the wiring board 140 including the heat-generation wirings 143a.

[Operation]

If the heat generator 120 generates heat, the heat is conveyed directly to the heat-generation wirings 143a. This heat is radially emitted around the heat-generation wirings 143a, and tends to be conveyed to the temperature sensor 130.

However, in the present modification, the suppressing portion 160 is disposed in the measurement-side directly under portion 130a, and the suppressing portion 160 includes at least one of the protection layer 160a, sealing portion 160b and air layer 160c.

The suppressing portion 160, which is disposed in this manner, suppresses the transfer of heat to the temperature sensor 130. Specifically, by the suppressing portion 160, the heat resistance from the heat-generation wirings 143a to the temperature sensor 130 via the measurement-side directly under portion 130a increases, and the heat flow, which is conveyed from the heat-generation wirings 143a to the temperature sensor 130, becomes smaller than the heat flow a3.

Moreover, since the heat flow a12, which is conveyed from the temperature sensor 130 to the lens frame 40, becomes smaller than the heat flow a2, the temperature difference b12 between the temperature sensor 130 and the lens frame 40 becomes smaller than the temperature difference b2.

The suppressing portion 160 decreases the direct influence of the heat, which is generated from the heat generator 120, upon the temperature sensor 130 via the wiring board 140, and the measurement accuracy of the temperature sensor 130 is enhanced.

The base layer 141 is formed of a resin, and the coefficient of thermal conductivity of the base layer 141 is low. The base layer 141 serves also as the suppressing portion 160, and, in other words, the suppressing portion 160 includes the base layer 141. Thus, even if the heat is conveyed to the base layer 141, the transfer of the heat from the base layer 141 to the temperature sensor 130 is suppressed. As a result, the measurement accuracy of the temperature sensor 130 is enhanced.

[Advantageous Effects]

In this manner, in the present modification, in the state in which the heat-generation wirings 143a are disposed in the measurement-side directly under portion 130a included in the vicinity of the temperature sensor 130, the suppressing portion 160 is disposed in the measurement-side directly under portion 130a included in the second heat transfer path 172 extending from the heat-generation wirings 143a to the temperature sensor 130, and the suppressing portion 160 suppresses heat transfer from the heat-generation wirings 143a to the temperature sensor 130 in the second heat transfer path 172.

Thereby, in the present modification, when the heat generator 120 generates heat, it is possible to suppress the transfer of the heat to the temperature sensor 130 via the heat-generation wirings 143a. Thereby, in this modification, the measurement accuracy of the temperature sensor 130 can be enhanced.

In the present modification, the heat resistance of the heat transfer path from the heat generator 120 to the lens frame 40 is smaller than the heat resistance of the second heat transfer path 172. In this modification, the heat resistance of the heat transfer path from the heat generator 120 to the temperature sensor 130 via the lens frame 40 is smaller than the heat resistance of the heat transfer path from the heat generator 120 to the temperature sensor 130 via the wiring board 140 including the heat-generation wirings 143a.

Specifically, in this modification, since the suppressing portion 160 is disposed in the second heat transfer path 172, a great amount of heat can be suppressed by the suppressing portion 160, and it is possible to suppress the transfer of the heat, which is generated from the heat generator 120, to the second heat transfer path 172 than the lens frame 40.

In the present modification, the suppressing portion 160 is disposed in the measurement-side directly under portion 130a. Thus, when the heat generator 120 generates heat, it is possible to surely suppress the transfer of the heat to the temperature sensor 130 via the heat-generation wirings 143a.

Second Modification of the First Embodiment

Hereinafter, referring to FIG. 8A and FIG. 8B, a second modification of the first embodiment is described. Incidentally, in FIG. 8A, depiction of the suppressing portion 160 is omitted to clarify the illustration.

In the first embodiment, parts of the measurement wirings 143b are disposed in the heat-generating-side directly under portion 120a. However, this is not intended to be restrictive.

[Positions of Heat-Generation Wring Portions 143a and Measurement Wirings 143b]

In the present modification, in the state in which the heat generator 120 and temperature sensor 130 are disposed on the wiring board 140, the measurement wirings 143b are disposed in the vicinity of the heat generator 120.

As illustrated in FIG. 8B, the vicinity of the heat generator 120 refers to, for example, an inside of a desired range of the heat generator 120, such as a range 170 of transfer of heat generated from the heat generator 120, and, to be more specific, the peripheral area of the heat generator 120. In other words, the measurement wirings 143b are disposed in the wiring board 140 at a position where heat generated from the heat generator 120 is transferred.

Next, an example of the vicinity of the heat generator 120 in the present modification is described.

In the present modification, as illustrated in FIG. 8A, like the first embodiment, for example, the heat generator 120 is disposed farther from the lens cover 31 (the distal end face of the distal end portion 15a) than the temperature sensor 130.

In this case, as illustrated in FIG. 8A, for example, the two wiring lines of the heat-generation wirings 143a are disposed to be sandwiched between one wiring line and another wiring line of the measurement wiring lines 143b in the width direction of the wiring board 140. For example, in the width direction of the wiring board 140, the distance between the wiring lines of the heat-generation wirings 143a is smaller than the distance between one wiring line of the heat-generation wirings 143a and one wiring line of the measurement wirings 143b, which neighbors this one wiring line of the heat-generation wirings 143a, and is smaller than the distance between the other wiring line of the heat-generation wirings 143a and the other wiring line of the measurement wirings 143b, which neighbors this other wiring line of the heat-generation wirings 143a. The distance between one wiring line of the heat-generation wirings 143a and one wiring line of the measurement wirings 143b, which neighbors this one wiring line of the heat-generation wirings 143a, is substantially equal to the distance between the other wiring line of the heat-generation wirings 143a and the other wiring line of the measurement wirings 143b, which neighbors this other wiring line of the heat-generation wirings 143a.

The heat-generation wirings 143a and the measurement wirings 143b, which are disposed as described above, are disposed symmetric with respect to the center axis of the heat generator 120 which is disposed along the longitudinal direction of the wiring board 140.

In addition, as illustrated in FIG. 8A and FIG. 8B, a part of the measurement wiring 143b is disposed in a lateral portion 120b of the heat generator 120. The lateral portion 120b indicates a space portion which includes a peripheral surface of the heat generator 120, neighbors the heat generator 120, and is located in the peripheral area of the heat generator 120. The lateral portion 120b is disposed inside the range 170 of transfer of heat generated from the heat generator 120. The measurement wiring 143b is disposed in the lateral portion 120b. As illustrated in FIG. 8A, in the width direction of the wiring board 140, a distance L1 between one wiring line of the measurement wirings 143b and the heat generator 120 is smaller than a distance L2 between one wiring line of the measurement wirings 143b and one wiring line of the heat-generation wirings 143a, which neighbors this one wiring line of the measurement wirings 143b.

In the measurement wirings 143b which are disposed so as to establish the distances L1 and L2, the lateral portion 120b, in which the measurement wiring 143b is disposed, is included in the above-described vicinity of the heat generator 120, for example, is located in the range 170 of transfer of heat generated from the heat generator 120, and is located in the peripheral area of the heat generator 120. In other words, the lateral portion 120b is disposed at a position where heat generated from the heat generator 120 is transferred, and the heat generated from the heat generator 120 is transferred to the lateral portion 120b.

[Suppressing Portion 160]

In the present modification, since a part of the measurement wiring 143b is disposed in the lateral portion 120b, the suppressing portion 160 needs to suppress the transfer of heat, which is generated from the heat generator 120, to a part of the measurement wiring 143b.

Thus, as illustrated in FIG. 8B, the suppressing portion 160 is disposed in a first heat transfer path 171 extending from the heat generator 120 to the measurement wiring 143b. The first heat transfer path 171 includes, for example, the lateral portion 120b, and indicates a path along which the heat generated from the heat generator 120 reaches the measurement wiring 143b. The suppressing portion 160, which is disposed in the first heat transfer path 171, suppresses the heat transfer from the heat generator 120 to the measurement wirings 143b. Thereby, the suppressing portion 160 suppresses the transfer of the heat, which is generated from the heat generator 120, to the temperature sensor 130 via the wiring board 140 including the wirings 143.

By the suppressing portion 160 which is disposed as described above, the heat resistance from the heat generator 120 to the measurement wiring 143b via the lateral portion 120b of the heat generator 120 increases, and the heat flow, which is conveyed from the heat generator 120 to the temperature sensor 130 via the lateral portion 120b of heat generator 120 and the wiring board 140 including the measurement wiring 143b, becomes smaller than the heat flow a3.

Furthermore, the heat flow a12, which is conveyed from the temperature sensor 130 to the lens frame 40, becomes smaller than the heat flow a2, thereby, the temperature difference b12 between the temperature sensor 130 and the lens frame 40 becomes smaller than the temperature difference b2.

Thus, the heat, which is generated from the heat generator 120, does not affect the temperature sensor 130, and the measurement accuracy of the temperature sensor 130 is enhanced.

Because of the above, the heat resistance of the heat transfer path from the heat generator 120 to the lens frame 40 is smaller than the heat resistance of the first heat transfer path 171. The heat resistance of the heat transfer path from the heat generator 120 to the temperature sensor 130 via the lens frame 40 is smaller than the heat resistance of the heat transfer path from the heat generator 120 to the temperature sensor 130 via the wiring board 140 including the measurement wirings 143*b*.

[Operation]

If the heat generator 120 generates heat, the heat is emitted radially around the heat generator 120. This heat tends to be conveyed, for example, from the heat generator 120 to the wiring board 140 including the measurement wiring 143*b* via the lateral portion 120*b* of the heat generator 120.

However, in the present modification, the suppressing portion 160 is disposed in the lateral portion 120*b*, and the suppressing portion 160 includes at least one of the protection layer 160*a*, sealing portion 160*b* and air layer 160*c*.

The suppressing portion 160, which is disposed in this manner, suppresses the transfer of heat to the measurement wirings 143*b*. Specifically, by the suppressing portion 160, the heat resistance from the heat generator 120 to the measurement wirings 143*b* via the lateral portion 120*b* of the heat generator 120 increases, and the heat flow, which is conveyed from the heat generator 120 to the temperature sensor 130 via the lateral portion 120*b* and the wiring board 140 including the measurement wirings 143*b*, becomes smaller than the heat flow a3.

Moreover, since the heat flow a12, which is conveyed from the temperature sensor 130 to the lens frame 40, becomes smaller than the heat flow a2, the temperature difference b12 between the temperature sensor 130 and the lens frame 40 becomes smaller than the temperature difference b2.

The suppressing portion 160 decreases the direct influence of the heat, which is generated from the heat generator 120, upon the temperature sensor 130 via the wiring board 140, and the measurement accuracy of the temperature sensor 130 is enhanced.

The base layer 141 is formed of a resin, and the coefficient of thermal conductivity of the base layer 141 is low. The base layer 141 serves also as the suppressing portion 160, and, in other words, the suppressing portion 160 includes the base layer 141. Thus, even if the heat is conveyed to the base layer 141, the transfer of the heat from the base layer 141 to the measurement wirings 143*b* is suppressed, and furthermore the transfer of the heat to the temperature sensor 130 is suppressed. As a result, the measurement accuracy of the temperature sensor 130 is enhanced.

[Advantageous Effects]

In this manner, in the present modification, in the state in which the measurement wirings 143*b* are disposed in the lateral portion 120*b* of the heat generator 120 included in the vicinity of the heat generator 120, the suppressing portion 160 is disposed in the lateral portion 120*b* of the heat generator 120 included in the first heat transfer path 171 extending from the heat generator 120 to the measurement wirings 143*b*, and suppresses heat transfer from the heat generator 120 to the measurement wirings 143*b* in the first heat transfer path 171.

Thereby, in the present modification, when the heat generator 120 generates heat, it is possible to suppress the transfer of the heat to the temperature sensor 130 via the measurement wirings 143*b* and the wiring board 140. Thereby, in this modification, the measurement accuracy of the temperature sensor 130 can be enhanced.

In the present modification, the heat resistance of the heat transfer path from the heat generator 120 to the lens frame 40 is smaller than the heat resistance of the first heat transfer path 171. In this modification, the heat resistance of the heat transfer path from the heat generator 120 to the temperature sensor 130 via the lens frame 40 is smaller than the heat resistance of the heat transfer path from the heat generator 120 to the temperature sensor 130 via the wiring board 140 including the measurement wirings 143*b*.

Specifically, in this modification, since the suppressing portion 160 is disposed in the first heat transfer path 171, a great amount of heat can be suppressed by the suppressing portion 160, and it is possible to suppress the transfer of the heat, which is generated from the heat generator 120, to the first heat transfer path 171 than the lens frame 40.

In the present modification, the suppressing portion 160 is disposed in the lateral portion 120*b* of the heat generator 120. Thus, when the heat generator 120 generates heat, it is possible to surely suppress the transfer of the heat to the temperature sensor 130 via the measurement wirings 143*b* and the wiring board 140.

Third Modification of the First Embodiment

Figure 9B:
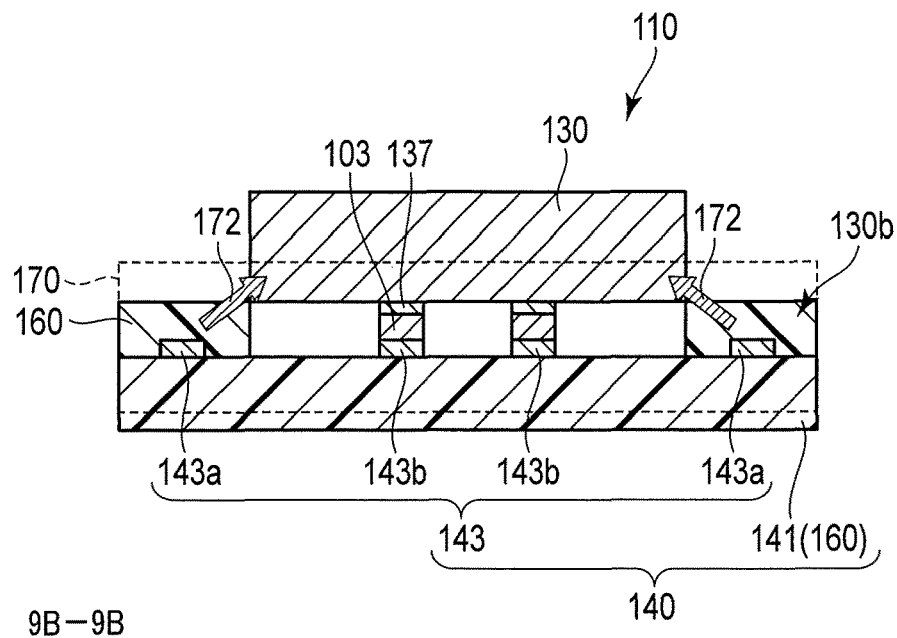
FIG. 9B is a cross-sectional view taken along line 9B-9B shown in FIG. 9A.

Hereinafter, referring to FIG. 9A and FIG. 9B, a third modification of the first embodiment is described. Incidentally, in FIG. 9A, depiction of the suppressing portion 160 is omitted to clarify the illustration.

In the first embodiment, parts of the measurement wirings 143*b* are disposed directly under the heat generator 120. However, this is not intended to be restrictive.

[Positions of Heat-Generation Wring Portions 143*a* and Measurement Wirings 143*b*]

In the state in which the heat generator 120 and temperature sensor 130 are disposed on the wiring board 140, the temperature sensor 130 may be disposed in the vicinity of the heat-generation wirings 143*a*.

As illustrated in FIG. 9B, the vicinity of the heat-generation wirings 143*a* refers to, for example, an inside of a desired range of the heat-generation wirings 143*a*, such as a range 170 of transfer of heat generated from the heat-generation wirings 143*a*, and, to be more specific, the peripheral area of the heat-generation wirings 143*a*. In other words, the temperature sensor 130 is disposed in the wiring board 140 at a position where heat generated from the heat-generation wirings 143*a* is transferred.

Next, an example of the vicinity of the temperature sensor 130 in the present modification is described.

In this case, as illustrated in FIG. 9A, the positions of disposition of the heat generator 120 and temperature sensor 130 may be reversed, compared to the first modification. Thus, for example, the temperature sensor 130 is disposed farther from the lens cover 31 (the distal end face of the distal end portion 15*a*) than the heat generator 120.

In addition, as illustrated in FIG. 9A, for example, the two wiring lines of the measurement wirings 143*b* are disposed to be sandwiched between one wiring line and the other wiring line of the heat-generation wiring lines 143*a* in the width direction of the wiring board 140. For example, in the width direction of the wiring board 140, the distance between the wiring lines of the measurement wirings 143*b* is smaller than the distance between one wiring line of the heat-generation wirings 143*a* and one wiring line of the measurement wirings 143*b*, which neighbors this one wiring line of the heat-generation wirings 143*a*, and is smaller than the distance between the other wiring line of the heat-generation wirings 143*a* and the other wiring line of the measurement wirings 143*b*, which neighbors this other wiring line of the heat-generation wirings 143*a*. The distance between one wiring line of the heat-generation wirings 143*a* and one wiring line of the measurement wirings 143*b*, which neighbors this one wiring line of the heat-generation wirings 143a, is substantially equal to the distance between the other wiring line of the heat-generation wirings 143a and the other wiring line of the measurement wirings 143b, which neighbors this other wiring line of the heat-generation wirings 143a.

The heat-generation wirings 143a and the measurement wirings 143b, which are disposed as described above, are disposed symmetric with respect to the center axis of the temperature sensor 130 which is disposed along the longitudinal direction of the wiring board 140.

In addition, as illustrated in FIG. 9A and FIG. 9B, a part of the heat-generation wiring 143a is disposed in a lateral portion 130b of the temperature sensor 130. The lateral portion 130b indicates a space portion which includes a peripheral surface of the temperature sensor 130, neighbors the temperature sensor 130, and is located in the peripheral area of the temperature sensor 130. The lateral portion 130b is disposed inside the range 170 of transfer of heat generated from the heat-generation wiring 143a. The heat-generation wiring 143a is disposed in the lateral portion 130b. As illustrated in FIG. 9A, in the width direction of the wiring board 140, a distance L3 between one wiring line of the heat-generation wirings 143a and the temperature sensor 130 is smaller than a distance L4 between one wiring line of the heat-generation wirings 143a and one wiring line of the measurement wirings 143b, which neighbors this one wiring line of the heat-generation wirings 143a.

In the heat-generation wirings 143a which are disposed so as to establish the distances L3 and L4, the lateral portion 130b, in which the heat-generation wiring 143a is disposed, is included in the above-described vicinity of the temperature sensor 130, for example, the lateral portion 130b is located in the range 170 of transfer of heat generated from the heat-generation wiring 143a, and is located in the peripheral area of the temperature sensor 130. In other words, the lateral portion 130b is disposed at a position where heat generated from the heat-generation wirings 143a is transferred, and the heat generated from the heat-generation wirings 143a is transferred to the lateral portion 130b.

[Suppressing Portion 160]

In the present modification, since a part of the heat-generation wiring 143a is disposed in the lateral portion 130b of the temperature sensor 130, the suppressing portion 160 needs to suppress the transfer of heat, which is generated from the heat-generation wirings 143a, to the temperature sensor 130.

Thus, as illustrated in FIG. 9B, the suppressing portion 160 is disposed in a second heat transfer path 172 extending from the heat-generation wiring 143a to the temperature sensor 130. The second heat transfer path 172 includes, for example, the lateral portion 130b, and indicates a path along which the heat generated from the heat-generation wiring 143a reaches the temperature sensor 130. The suppressing portion 160, which is disposed in the second heat transfer path 172, suppresses the transfer of heat from the heat-generation wiring 143a to the temperature sensor 130. Thereby, the suppressing portion 160 suppresses the transfer of the heat, which is generated from the heat-generation wiring 143a to the temperature sensor 130.

By the suppressing portion 160 which is disposed as described above, the heat resistance from the heat-generation wiring 43a to the temperature sensor 130 via the lateral portion 130b increases, and, in other words, the suppressing portion 160 suppresses the transfer of heat to the temperature sensor 130. The heat flow, which is conveyed from the heat-generation wiring 143a to the temperature sensor 130 via the lateral portion 130b, becomes smaller than the heat flow a3.

Furthermore, the heat flow a12, which is conveyed from the temperature sensor 130 to the lens frame 40, becomes smaller than the heat flow a2, thereby, the temperature difference b12 between the temperature sensor 130 and the lens frame 40 becomes smaller than the temperature difference b2.

Thus, the heat, which is generated from the heat generator 120, does not affect the temperature sensor 130, and the measurement accuracy of the temperature sensor 130 is enhanced.

Because of the above, the heat resistance of the heat transfer path from the heat generator 120 to the lens frame 40 is smaller than the heat resistance of the second heat transfer path 172. The heat resistance of the heat transfer path from the heat generator 120 to the temperature sensor 130 via the lens frame 40 is smaller than the heat resistance of the heat transfer path from the heat generator 120 to the temperature sensor 130 via the wiring board 140 including the heat-generation wirings 143a.

[Operation]

If the heat generator 120 generates heat, the heat generator 120 produces the heat radially around the heat generator 120. This heat tends to be conveyed, for example, from the heat generator 120 to the temperature sensor 130 via the heat-generation wirings 143a and the lateral portion 130b of the temperature sensor 130.

However, in the present modification, the suppressing portion 160 is disposed in the lateral portion 130b, and the suppressing portion 160 includes at least one of the protection layer 160a, sealing portion 160b and air layer 160c.

The suppressing portion 160, which is disposed in this manner, suppresses the transfer of heat to the temperature sensor 130. Specifically, by the suppressing portion 160, the heat resistance from the heat-generation wirings 143a to the temperature sensor 130 via the lateral portion 130b of the temperature sensor 130 increases, and the heat flow, which is conveyed from the heat-generation wirings 143a to the temperature sensor 130, becomes smaller than the heat flow a3.

Moreover, since the heat flow a12, which is conveyed from the temperature sensor 130 to the lens frame 40, becomes smaller than the heat flow a2, the temperature difference b12 between the temperature sensor 130 and the lens frame 40 becomes smaller than the temperature difference b2.

The suppressing portion 160 decreases the direct influence of the heat, which is generated from the heat generator 120, upon the temperature sensor 130 via the wiring board 140, and the measurement accuracy of the temperature sensor 130 is enhanced.

The base layer 141 is formed of a resin, and the coefficient of thermal conductivity of the base layer 141 is low. The base layer 141 serves also as the suppressing portion 160, and, in other words, the suppressing portion 160 includes the base layer 141. Thus, even if the heat is conveyed to the base layer 141, the transfer of the heat from the base layer 141 to the measurement wirings 143b is suppressed, and furthermore the transfer of the heat to the temperature sensor 130 is suppressed. As a result, the measurement accuracy of the temperature sensor 130 is enhanced.

[Advantageous Effects]

In this manner, in the present modification, in the state in which the heat-generation wirings 143a are disposed in the lateral portion 130b of the temperature sensor 130 included in the vicinity of the temperature sensor 130, the suppressing portion 160 is disposed in the lateral portion 130b of the temperature sensor 130 included in the second heat transfer path 172 extending from the heat-generation wirings 143a to the temperature sensor 130, and the suppressing portion 160 suppresses the heat transfer from the heat-generation wirings 143a to the temperature sensor 130 in the second heat transfer path 172.

Thereby, in the present modification, when the heat generator 120 generates heat, it is possible to suppress the transfer of the heat to the temperature sensor 130 via the heat-generation portion 143a. Thereby, in this modification, the measurement accuracy of the temperature sensor 130 can be enhanced.

In the present modification, the heat resistance of the heat transfer path from the heat generator 120 to the lens frame 40 is smaller than the heat resistance of the second heat transfer path 172. In this modification, the heat resistance of the heat transfer path from the heat generator 120 to the temperature sensor 130 via the lens frame 40 is smaller than the heat resistance of the heat transfer path from the heat generator 120 to the temperature sensor 130 via the wiring board 140 including the heat-generation wirings 143a.

Specifically, in this modification, since the suppressing portion 160 is disposed in the second heat transfer path 172, a great amount of heat can be suppressed by the suppressing portion 160, and it is possible to suppress the transfer of the heat, which is generated from the heat generator 120, to the second heat transfer path 172 than to the lens frame 40.

In the present modification, since the suppressing portion 160 is disposed in the lateral portion 130b of the temperature sensor 130, when the heat generator 120 generates heat, it is possible to surely suppress the transfer of the heat to the temperature sensor 130 via the heat-generation wirings 143a.

Second Embodiment

In the first embodiment, the heat-generation wirings 143a and the measurement wirings 143b are disposed on a plane in common in the base layer 141. However, this is not restrictive. Only different points from the first embodiment will be described below.

Figure 10A:
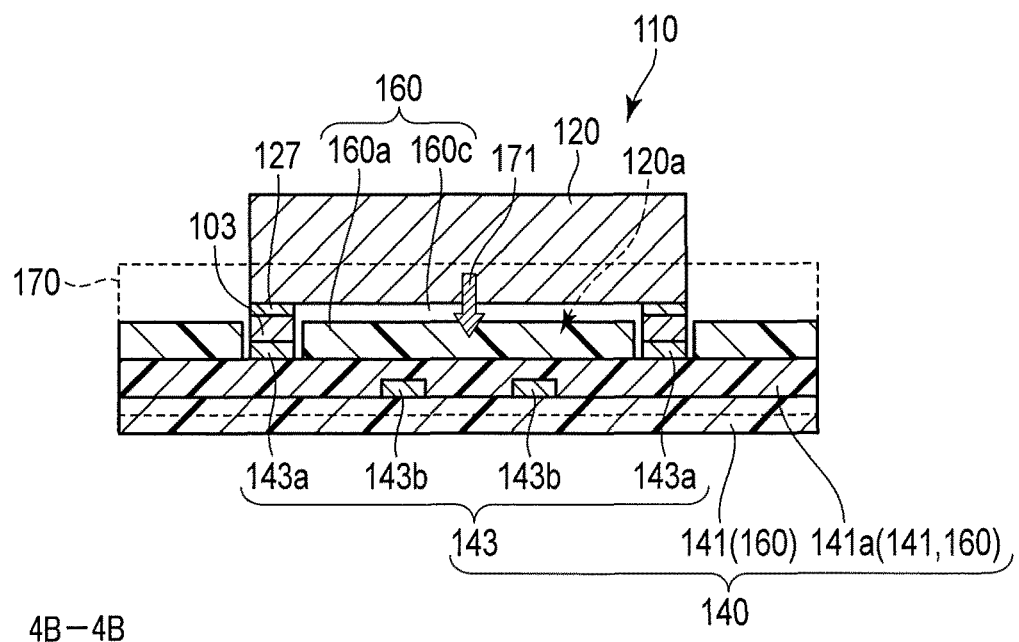
FIG. 10A is a cross-sectional view taken along line 4B-4B, illustrating a second embodiment.

As illustrated in FIG. 10A, the heat-generation wirings 143a and the measurement wirings 143b may be disposed on different planes in the base layer 141.

In this case, the wiring board 140 further includes an intermediate layer 141a which is formed as a portion of the base layer 141 and is stacked on the base layer 141.

One of the heat generator 120 and the temperature sensor 130 is disposed on one of the base layer 141 and the intermediate layer 141a, and another of the heat generator 120 and the temperature sensor 130 is disposed on another of the base layer 141 and the intermediate layer 141a. In accordance with the positions of the heat generator 120 and the temperature sensor 130, the heat-generation wirings 143a are disposed on the base layer 141 or intermediately layer 141a, and the measurement wirings 143b are disposed on the intermediate layer 141a or base layer 141.

In the meantime, in the present embodiment, like the first embodiment, a part of the measurement wiring 143b is disposed in the heat-generating-side directly under portion 120a which is disposed directly under the heat generator 120. Thereby, the same advantageous effects as in the first embodiment can be obtained.

As illustrated in FIG. 10B, in a first modification of the present embodiment, like the first modification of the first embodiment, a part of the heat-generation wiring 143a may be disposed in the measurement-side directly under portion 130a which is disposed directly under the temperature sensor 130. Thereby, the same advantageous effects as in the first modification of the first embodiment can be obtained.

As illustrated in FIG. 10C, in a second modification of the present embodiment, like the second modification of the first embodiment, a part of the measurement wiring 143b may be disposed in the lateral portion 120b of the heat generator 120. Thereby, the same advantageous effects as in the second modification of the first embodiment can be obtained.

Figure 10D:
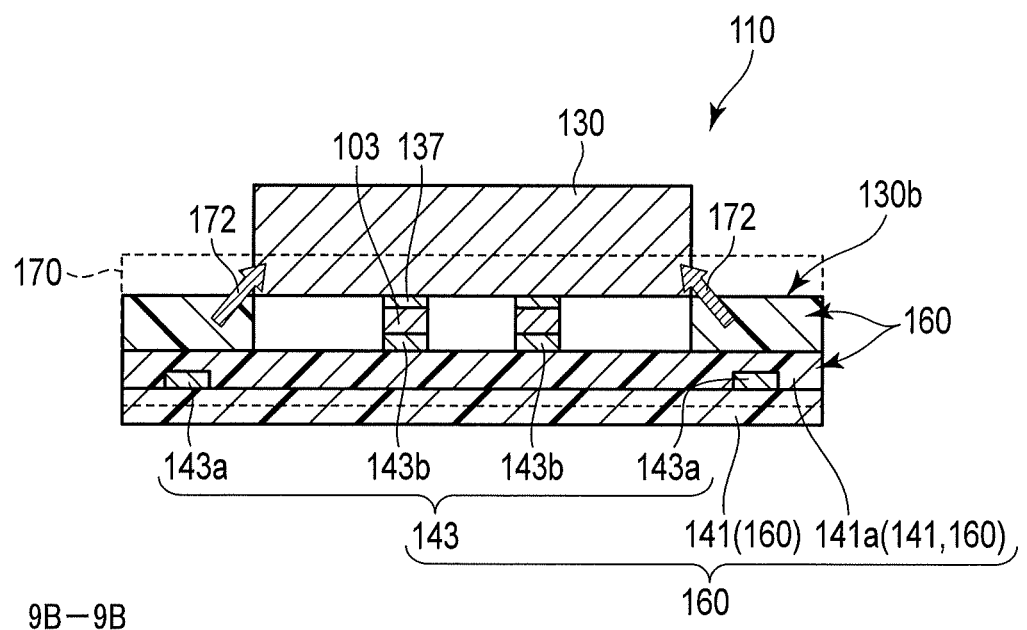
FIG. 10D is a cross-sectional view taken along line 9B-9B, illustrating a third modification of the second embodiment.

As illustrated in FIG. 10D, in a third modification of the present embodiment, like the third modification of the first embodiment, a part of the heat-generation wiring 143a may be disposed in the lateral portion 130b of the temperature sensor 130. Thereby, the same advantageous effects as in the third modification of the first embodiment can be obtained.

The above is not restrictive, however. It should suffice if the heat-generation wirings 143a and the measurement wirings 143b are disposed on different planes in the base layer 141. Thus, for example, the heat-generation wirings 143a may be disposed on the front surface of the base layer 141, and the measurement wirings 143b may be disposed on the back surface of the base layer 141.

The present invention is not limited directly to the above-described embodiments. At the stage of practicing the invention, the structural elements may be modified and embodied without departing from the spirit of the invention. Various inventions may be made by suitably combining a plurality of structural elements disclosed in the embodiments.

What is claimed is:

1. An endoscope antifogging unit which is disposed in an inside of a distal end portion of an endoscope insertion section having a lens frame and is configured to prevent fogging occurring on an optical member disposed in the inside of the distal end portion, the endoscope antifogging unit comprising:
  a heat generator configured to heat the inside by heat generation;
  a temperature sensor configured to measure a temperature of the inside;
  a wiring board comprising:
    a base layer, and
    wirings disposed on the base layer, the wirings comprising:
      a heat-generation wiring connected to the heat generator and
      a measurement wiring connected to the temperature sensor,
    the wiring board being configured such that, in a state in which the heat generator and the temperature sensor are disposed on the wiring board, the measurement wiring is disposed in a vicinity of the heat generator, or the temperature sensor is disposed in a vicinity of the heat-generation wiring; and
  a suppressing portion including at least one of a protection layer configured to protect a surface of the wirings in such a manner as to cover the surface of the wirings, a sealing material configured to seal the wirings in such a manner as to cover the wirings, and an air layer, the suppressing portion being disposed in either a first heat transfer path extending from the heat generator to the measurement wiring or a second heat transfer path extending from the heat-generation wiring to the temperature sensor,
  wherein the suppressing portion being configured to suppress heat transfer, in cooperation with the base layer, from the heat generator to the measurement wiring in the first heat transfer path, or to suppress heat transfer from the heat-generation wiring to the temperature sensor in the second heat transfer path, and the suppressing portion is disposed between the measurement wiring and the heat generator where the measurement wiring is disposed between the base layer and the heat generator, or the suppressing portion is disposed between the heat-generation wiring and the temperature sensor where the heat-generation wiring is disposed between the base layer and the temperature sensor.

2. The endoscope antifogging unit according to claim 1, wherein the heat generator and the temperature sensor are mounted on the lens frame the lens frame being disposed in the inside of the distal end portion, the lens frame being configured to hold the optical member and to transfer heat of the heat generator, and a heat resistance of a heat transfer path from the heat generator to the lens frame is smaller than a heat resistance of the first heat transfer path or a heat resistance of the second heat transfer path.

3. The endoscope antifogging unit according to claim 1, wherein the heat generator and the temperature sensor are mounted on the lens frame the lens frame being disposed in the inside of the distal end portion, the lens frame being configured to hold the optical member and to transfer heat of the heat generator, and a heat resistance of a heat transfer path from the heat generator to the temperature sensor via the lens frame is smaller than a heat resistance of a heat transfer path from the heat generator to the temperature sensor via the wiring board including the measurement wiring, or a heat resistance of a heat transfer path from the heat generator to the temperature sensor via the wiring board including the heat-generation wiring.

4. The endoscope antifogging unit according to claim 1, wherein the heat-generation wiring and the measurement wiring are disposed on a plane in common in the base layer, and the measurement wiring is disposed directly under the heat generator, or the heat-generation wiring is disposed directly under the temperature sensor.

5. The endoscope antifogging unit according to claim 1, wherein the heat-generation wiring and the measurement wiring are disposed on a plane in common in the base layer, and the measurement wiring is disposed in a lateral portion of the heat generator, or the heat-generation wiring is disposed in a lateral portion of the temperature sensor.

6. The endoscope antifogging unit according to claim 1, wherein the heat-generation wiring and the measurement wiring are disposed on different planes in the base layer, and the measurement wiring is disposed directly under the heat generator, or the heat-generation wiring is disposed directly under the temperature sensor.

7. The endoscope antifogging unit according to claim 1, wherein the heat-generation wiring and the measurement wiring are disposed on different planes in the base layer, and the measurement wiring is disposed in a lateral portion of the heat generator, or the heat-generation wiring is disposed in a lateral portion of the temperature sensor.

8. An endoscope comprising:

an endoscope insertion section including a distal end portion;

an optical member disposed in an inside of the distal end portion; and the endoscope antifogging unit according to claim 1, the endoscope antifogging unit being disposed in the inside of the distal end portion and being configured to prevent fogging from occurring on the optical member.

9. An insertion section for use with an endoscope, the insertion section comprising:

a distal end portion having a lens frame;

an optical member disposed in an inside of the distal end portion; and an endoscope antifogging unit configured to prevent fogging occurring on an optical member, the endoscope antifogging unit comprising:

a heat generator configured to heat the inside by heat generation;

a temperature sensor configured to measure a temperature of the inside;

a wiring board comprising:

a base layer, and wirings disposed on the base layer, the wirings comprising:

a heat-generation wiring connected to the heat generator; and a measurement wiring connected to the temperature sensor, the wiring board being configured such that, in a state in which the heat generator and the temperature sensor are disposed on the wiring board, the measurement wiring is disposed in a vicinity of the heat generator, or the temperature sensor is disposed in a vicinity of the heat-generation wiring; and a suppressing portion including at least one of a protection layer configured to protect a surface of the wirings in such a manner as to cover the surface of the wirings, a sealing material configured to seal the wirings in such a manner as to cover the wirings, and an air layer, the suppressing portion being disposed in either a first heat transfer path extending from the heat generator to the measurement wiring or a second heat transfer path extending from the heat-generation wiring to the temperature sensor, wherein the suppressing portion being configured to suppress heat transfer, in cooperation with the base layer, from the heat generator to the measurement wiring in the first heat transfer path, or to suppress heat transfer from the heat-generation wiring to the temperature sensor in the second heat transfer path, and the suppressing portion is disposed between the measurement wiring and the heat generator where the measurement wiring is disposed between the base layer and the heat generator, or the suppressing portion is disposed between the heat-generation wiring and the temperature sensor where the heat-generation wiring is disposed between the base layer and the temperature sensor.

* * * * *